(12) United States Patent
Fischer et al.

(10) Patent No.: US 11,957,426 B2
(45) Date of Patent: *Apr. 16, 2024

(54) INPUT STACKS FOR ROBOTIC SURGICAL TOOLS

(71) Applicant: Cilag GmbH International, Zug (CH)

(72) Inventors: Austin Michael Fischer, Cincinnati, OH (US); Jason Alan Hill, Loveland, OH (US)

(73) Assignee: Cilag GmbH International, Zug (CH)

( * ) Notice: Subject to any disclaimer, the term of this patent is extended or adjusted under 35 U.S.C. 154(b) by 369 days.

This patent is subject to a terminal disclaimer.

(21) Appl. No.: 17/313,503

(22) Filed: May 6, 2021

(65) Prior Publication Data
US 2022/0354604 A1 Nov. 10, 2022

(51) Int. Cl.
*A61B 34/00* (2016.01)
*A61B 34/37* (2016.01)
*A61B 34/30* (2016.01)

(52) U.S. Cl.
CPC .............. *A61B 34/71* (2016.02); *A61B 34/37* (2016.02); *A61B 2034/301* (2016.02); *A61B 2034/302* (2016.02)

(58) Field of Classification Search
CPC .............. A61B 34/71; A61B 2034/715; A61B 2017/00323; B25J 9/104; B25J 9/1045; B25J 15/0233; B25J 15/0293; F16H 2007/0865
See application file for complete search history.

(56) References Cited

U.S. PATENT DOCUMENTS

| 11,723,737 | B2 * | 8/2023 | Beckman | A61B 17/29 606/1 |
| 2021/0045825 | A1 * | 2/2021 | Lee | A61B 17/00234 |
| 2021/0059718 | A1 * | 3/2021 | Karam | A61B 17/3423 |

* cited by examiner

*Primary Examiner* — Bobby Rushing, Jr.
(74) *Attorney, Agent, or Firm* — Vorys, Sater, Seymour and Pease, LLP

(57) ABSTRACT

A robotic surgical tool includes an elongate shaft extendable through a handle, a drive cable extending along a portion of the shaft, and an actuation system housed within the handle and including an input stack having first and second ends. The input stack includes a drive input arranged at the first end, and an accumulator arranged between the first and second ends and including a differential body defining upper and lower redirect surfaces, and a redirect feature offset from the upper and lower redirect surfaces, wherein the drive cable is threaded through the upper and lower redirect surfaces and the redirect feature, and wherein actuating the actuation system rotates the input stack and thereby acts on the drive cable to cause one or more operations of the surgical tool.

20 Claims, 18 Drawing Sheets

INPUT STACKS FOR ROBOTIC SURGICAL TOOLS

TECHNICAL FIELD

The systems and methods disclosed herein are directed to robotic surgical tools and, more particularly to, input stacks used in cable-based actuation systems of robotic surgical tools.

BACKGROUND

Minimally invasive surgical (MIS) instruments are often preferred over traditional open surgical devices due to the reduced post-operative recovery time and minimal scarring. The most common MIS procedure may be endoscopy, and the most common form of endoscopy is laparoscopy, in which one or more small incisions are formed in the abdomen of a patient and a trocar is inserted through the incision to form a pathway that provides access to the abdominal cavity. The cannula and sealing system of the trocar are used to introduce various instruments and tools into the abdominal cavity, as well as to provide insufflation to elevate the abdominal wall above the organs. The instruments can be used to engage and/or treat tissue in a number of ways to achieve a diagnostic or therapeutic effect.

Each surgical tool typically includes an end effector arranged at its distal end. Example end effectors include clamps, graspers, scissors, staplers, suction irrigators, blades (i.e., RF), and needle holders, and are similar to those used in conventional (open) surgery except that the end effector of each tool is separated from its handle by an approximately 12-inch long shaft. A camera or image capture device, such as an endoscope, is also commonly introduced into the abdominal cavity to enable the surgeon to view the surgical field and the operation of the end effectors during operation. The surgeon is able to view the procedure in real-time by means of a visual display in communication with the image capture device.

Various robotic systems have recently been developed to assist in MIS procedures. Robotic systems can allow for more intuitive hand movements by maintaining natural eye-hand axis. Robotic systems can also allow for more degrees of freedom in movement by including a "wrist" joint that creates a more natural hand-like articulation and allows for access to hard to reach spaces. The instrument's end effector can be articulated (moved) using motors and actuators forming part of a computerized motion system. A user (e.g., a surgeon) is able to remotely operate an instrument's end effector by grasping and manipulating in space one or more controllers that communicate with an instrument driver coupled to the surgical instrument. User inputs are processed by a computer system incorporated into the robotic surgical system and the instrument driver responds by actuating the motors and actuators of the motion system. Moving drive cables, rods, and/or other mechanical mechanisms causes the end effector to articulate to desired positions and configurations.

In some robotic surgical systems, the drive cables are routed through actuation systems that include a rotatable input stack. Conventional input stacks are made of several component part, which increases the complexity and cost of the input stack. What is needed is less complex and costly input stacks.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

Aspects of the present disclosure may be integrated into a robotically-enabled medical system capable of performing a variety of medical procedures, including both minimally invasive (e.g., laparoscopy) and non-invasive (e.g., endoscopy) procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance, to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto, as such concepts may have applicability throughout the entire specification.

A. Robotic System—Cart.

Figure 1:
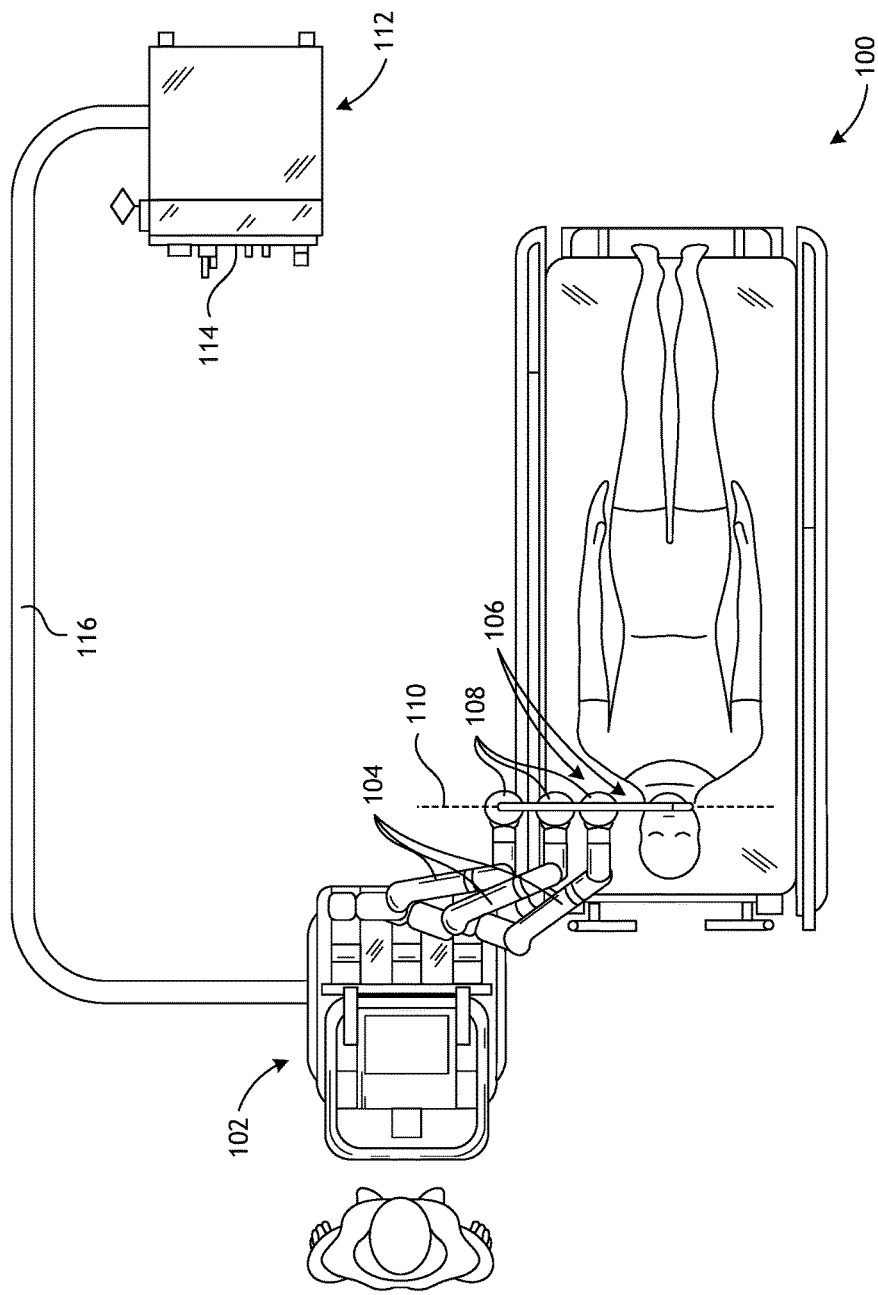
FIG. 1 illustrates an embodiment of a cart-based robotic system arranged for diagnostic and/or therapeutic bronchoscopy procedure(s).

The robotically-enabled medical system may be configured in a variety of ways depending on the particular procedure. FIG. 1 illustrates an embodiment of a cart-based robotically-enabled system 100 arranged for a diagnostic and/or therapeutic bronchoscopy procedure. For a bronchoscopy procedure, the robotic system 100 may include a cart 102 having one or more robotic arms 104 (three shown) to deliver a medical instrument (alternately referred to as a "surgical tool"), such as a steerable endoscope 106 (e.g., a procedure-specific bronchoscope for bronchoscopy), to a natural orifice access point (i.e., the mouth of the patient) to deliver diagnostic and/or therapeutic tools. As shown, the cart 102 may be positioned proximate to the patient's upper torso in order to provide access to the access point. Similarly, the robotic arms 104 may be actuated to position the bronchoscope relative to the access point. The arrangement in FIG. 1 may also be utilized when performing a gastrointestinal (GI) procedure with a gastroscope, a specialized endoscope for GI procedures.

Once the cart 102 is properly positioned adjacent the patient, the robotic arms 104 are operated to insert the steerable endoscope 106 into the patient robotically, manually, or a combination thereof. The steerable endoscope 106 may comprise at least two telescoping parts, such as an inner leader portion and an outer sheath portion, where each portion is coupled to a separate instrument driver of a set of instrument drivers 108. As illustrated, each instrument driver 108 is coupled to the distal end of a corresponding one of the robotic arms 104. This linear arrangement of the instrument drivers 108, which facilitates coaxially aligning the leader portion with the sheath portion, creates a "virtual rail" 110 that may be repositioned in space by manipulating the robotic arms 104 into different angles and/or positions. Translation of the instrument drivers 108 along the virtual rail 110 telescopes the inner leader portion relative to the outer sheath portion, thus effectively advancing or retracting the endoscope 106 relative to the patient.

As illustrated, the virtual rail 110 (and other virtual rails described herein) is depicted in the drawings using dashed lines, thus not constituting any physical structure of the system 100. The angle of the virtual rail 110 may be adjusted, translated, and pivoted based on clinical application or physician preference. For example, in bronchoscopy, the angle and position of the virtual rail 110 as shown represents a compromise between providing physician access to the endoscope 106 while minimizing friction that results from bending the endoscope 106 into the patient's mouth.

After insertion into the patient's mouth, the endoscope 106 may be directed down the patient's trachea and lungs using precise commands from the robotic system 100 until reaching a target destination or operative site. In order to enhance navigation through the patient's lung network and/or reach the desired target, the endoscope 106 may be manipulated to telescopically extend the inner leader portion from the outer sheath portion to obtain enhanced articulation and greater bend radius. The use of separate instrument drivers 108 also allows the leader portion and sheath portion to be driven independent of each other.

For example, the endoscope 106 may be directed to deliver a biopsy needle to a target, such as, for example, a lesion or nodule within the lungs of a patient. The needle may be deployed down a working channel that runs the length of the endoscope 106 to obtain a tissue sample to be analyzed by a pathologist. Depending on the pathology results, additional tools may be deployed down the working channel of the endoscope for additional biopsies. After identifying a tissue sample to be malignant, the endoscope 106 may endoscopically deliver tools to resect the potentially cancerous tissue. In some instances, diagnostic and therapeutic treatments can be delivered in separate procedures. In those circumstances, the endoscope 106 may also be used to deliver a fiducial marker to "mark" the location of a target nodule as well. In other instances, diagnostic and therapeutic treatments may be delivered during the same procedure.

The system 100 may also include a movable tower 112, which may be connected via support cables to the cart 102 to provide support for controls, electronics, fluidics, optics, sensors, and/or power to the cart 102. Placing such functionality in the tower 112 allows for a smaller form factor cart 102 that may be more easily adjusted and/or repositioned by an operating physician and his/her staff. Additionally, the division of functionality between the cart/table and the support tower 112 reduces operating room clutter and facilitates improving clinical workflow. While the cart 102 may be positioned close to the patient, the tower 112 may alternatively be stowed in a remote location to stay out of the way during a procedure.

In support of the robotic systems described above, the tower 112 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 112 or the cart 102, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, motors in the joints of the robotic arms 104 may position the arms into a certain posture or angular orientation.

The tower 112 may also include one or more of a pump, flow meter, valve control, and/or fluid access in order to provide controlled irrigation and aspiration capabilities to the system 100 that may be deployed through the endoscope 106. These components may also be controlled using the computer system of the tower 112. In some embodiments, irrigation and aspiration capabilities may be delivered directly to the endoscope 106 through separate cable(s).

The tower 112 may include a voltage and surge protector designed to provide filtered and protected electrical power to the cart 102, thereby avoiding placement of a power transformer and other auxiliary power components in the cart 102, resulting in a smaller, more moveable cart 102.

The tower 112 may also include support equipment for sensors deployed throughout the robotic system 100. For example, the tower 112 may include opto-electronics equipment for detecting, receiving, and processing data received from optical sensors or cameras throughout the robotic system 100. In combination with the control system, such opto-electronics equipment may be used to generate real-time images for display in any number of consoles deployed throughout the system, including in the tower 112. Similarly, the tower 112 may also include an electronic subsystem for receiving and processing signals received from deployed electromagnetic (EM) sensors. The tower 112 may also be used to house and position an EM field generator for detection by EM sensors in or on the medical instrument.

The tower 112 may also include a console 114 in addition to other consoles available in the rest of the system, e.g., a console mounted to the cart 102. The console 114 may include a user interface and a display screen (e.g., a touchscreen) for the physician operator. Consoles in the system 100 are generally designed to provide both robotic controls as well as pre-operative and real-time information of the procedure, such as navigational and localization information of the endoscope 106. When the console 114 is not the only console available to the physician, it may be used by a second operator, such as a nurse, to monitor the health or vitals of the patient and the operation of system, as well as provide procedure-specific data, such as navigational and localization information. In other embodiments, the console 114 may be housed in a body separate from the tower 112.

The tower 112 may be coupled to the cart 102 and endoscope 106 through one or more cables 116 connections. In some embodiments, support functionality from the tower 112 may be provided through a single cable 116 extending to the cart 102, thus simplifying and de-cluttering the operating room. In other embodiments, specific functionality may be coupled in separate cabling and connections. For example, while power may be provided through a single power cable to the cart 102, support for controls, optics, fluidics, and/or navigation may be provided through one or more separate cables.

Figure 2:
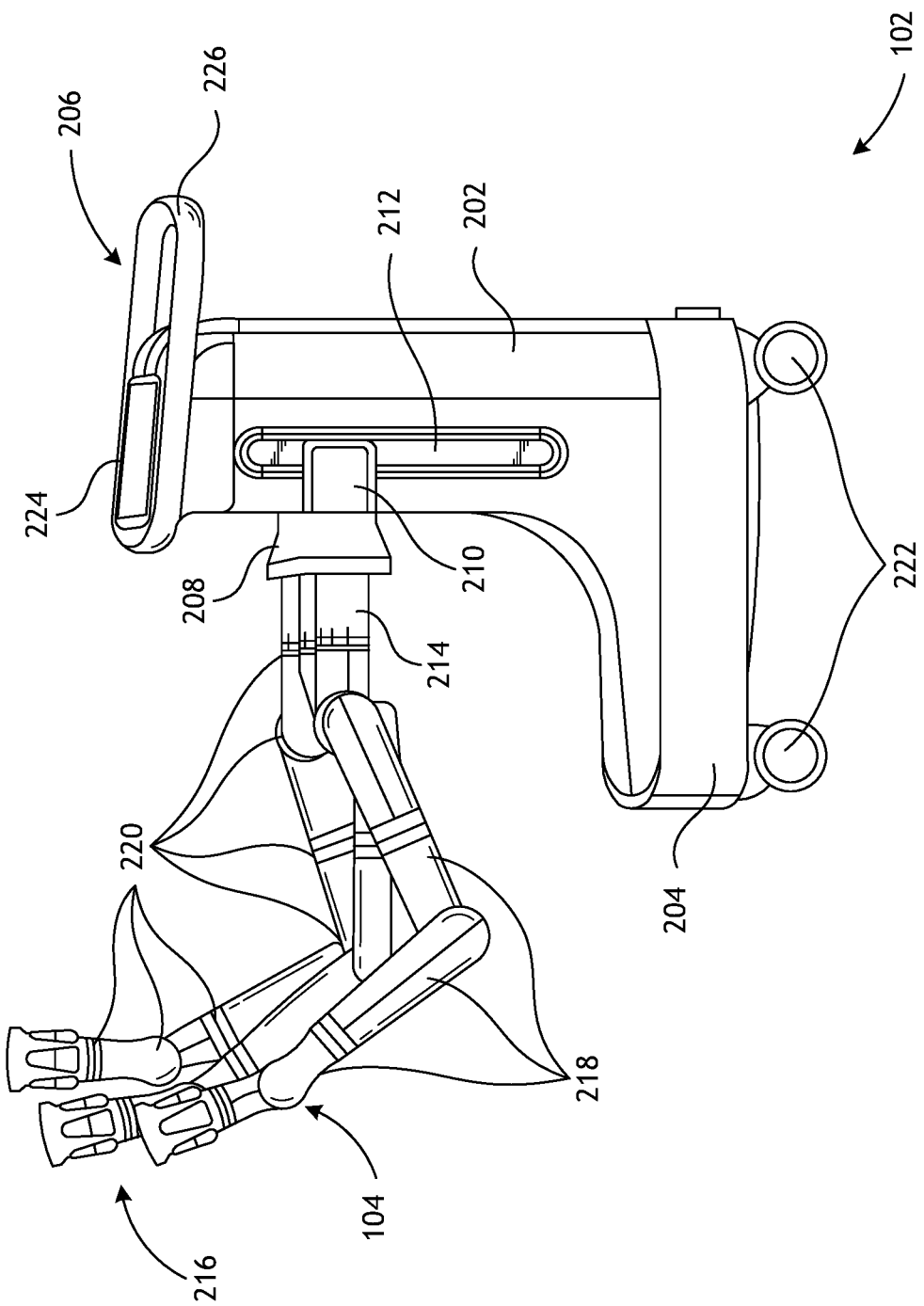
FIG. 2 depicts further aspects of the robotic system of FIG. 1.

FIG. 2 provides a detailed illustration of an embodiment of the cart 102 from the cart-based robotically-enabled system 100 of FIG. 1. The cart 102 generally includes an elongated support structure 202 (also referred to as a "column"), a cart base 204, and a console 206 at the top of the column 202. The column 202 may include one or more carriages, such as a carriage 208 (alternatively "arm support") for supporting the deployment of the robotic arms 104. The carriage 208 may include individually configurable arm mounts that rotate along a perpendicular axis to adjust the base 214 of the robotic arms 104 for better positioning relative to the patient. The carriage 208 also includes a carriage interface 210 that allows the carriage 208 to vertically translate along the column 202.

The carriage interface 210 is connected to the column 202 through slots, such as slot 212, that are positioned on opposite sides of the column 202 to guide the vertical translation of the carriage 208. The slot 212 contains a vertical translation interface to position and hold the carriage 208 at various vertical heights relative to the cart base 204. Vertical translation of the carriage 208 allows the cart 102 to adjust the reach of the robotic arms 104 to meet a variety of table heights, patient sizes, and physician preferences. Similarly, the individually configurable arm mounts on the carriage 208 allow a base 214 of the robotic arms 104 to be angled in a variety of configurations.

In some embodiments, the slot 212 may be supplemented with slot covers (not shown) that are flush and parallel to the slot surface to prevent dirt and fluid ingress into the internal chambers of the column 202 and the vertical translation interface as the carriage 208 vertically translates. The slot covers may be deployed through pairs of spring spools positioned near the vertical top and bottom of the slot 212. The covers are coiled within the spools until deployed to extend and retract from their coiled state as the carriage 208 vertically translates up and down. The spring-loading of the spools provides force to retract the cover into a spool when carriage 208 translates towards the spool, while also maintaining a tight seal when the carriage 208 translates away from the spool. The covers may be connected to the carriage 208 using, for example, brackets in the carriage interface 210 to ensure proper extension and retraction of the cover as the carriage 208 translates.

The column 202 may internally comprise mechanisms, such as gears and motors, which are designed to use a vertically aligned lead screw to translate the carriage 208 in a mechanized fashion in response to control signals generated in response to user inputs, e.g., inputs from the console 206.

The robotic arms 104 may generally comprise robotic arm bases 214 and end effectors 216 (three shown), separated by a series of linkages 218 connected by a corresponding series of joints 220, each joint 220 including an independent actuator, and each actuator including an independently controllable motor. Each independently controllable joint 220 represents an independent degree of freedom available to the corresponding robotic arm 104. In the illustrated embodiment, each arm 104 has seven joints 220, thus providing seven degrees of freedom. A multitude of joints 220 result in a multitude of degrees of freedom, allowing for "redundant" degrees of freedom. Redundant degrees of freedom allow the robotic arms 104 to position their respective end effectors 216 at a specific position, orientation, and trajectory in space using different linkage positions and joint angles. This allows for the system 100 to position and direct a medical instrument from a desired point in space while allowing the physician to move the arm joints 220 into a clinically advantageous position away from the patient to create greater access, while avoiding arm collisions.

The cart base 204 balances the weight of the column 202, the carriage 208, and the arms 104 over the floor. Accordingly, the cart base 204 houses heavier components, such as electronics, motors, power supply, as well as components that either enable movement and/or immobilize the cart. For example, the cart base 204 includes rolling casters 222 that allow for the cart to easily move around the room prior to a procedure. After reaching an appropriate position, the casters 222 may be immobilized using wheel locks to hold the cart 102 in place during the procedure.

Positioned at the vertical end of the column 202, the console 206 allows for both a user interface for receiving user input and a display screen (or a dual-purpose device such as, for example, a touchscreen 224) to provide the physician user with both pre-operative and intra-operative data. Potential pre-operative data on the touchscreen 224 may include pre-operative plans, navigation and mapping data derived from pre-operative computerized tomography (CT) scans, and/or notes from pre-operative patient interviews. Intra-operative data on the touchscreen 224 may include optical information provided from the tool, sensor and coordinate information from sensors, as well as vital patient statistics, such as respiration, heart rate, and/or pulse. The console 206 may be positioned and tilted to allow a physician to access the console from the side of the column 202 opposite carriage 208. From this position, the physician may view the console 206, the robotic arms 104, and the patient while operating the console 206 from behind the cart 102. As shown, the console 206 also includes a handle 226 to assist with maneuvering and stabilizing cart 102.

Figure 3A:
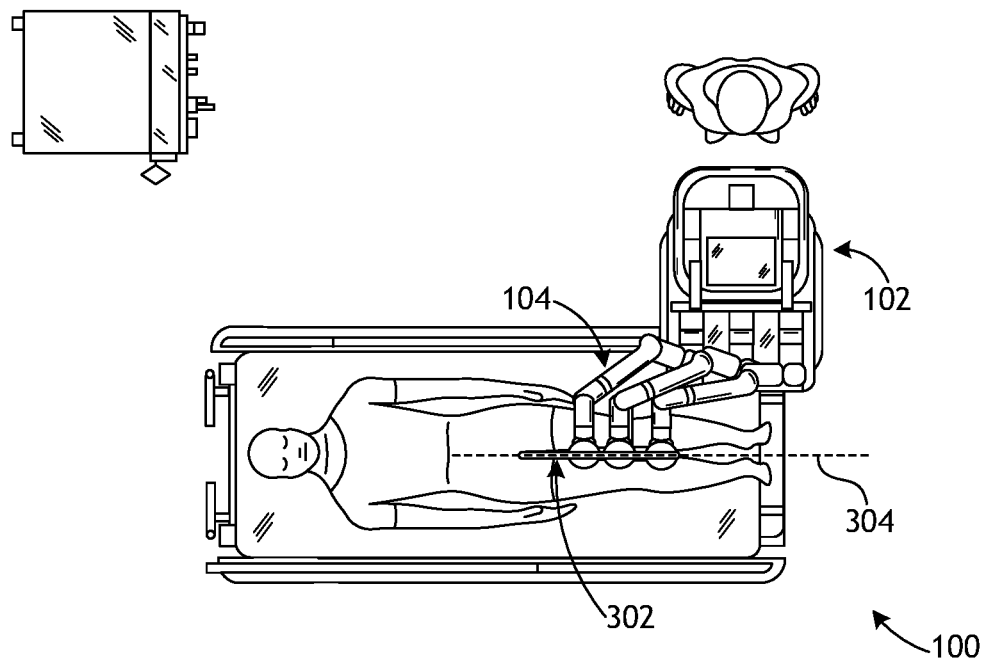
FIG. 3A illustrates an embodiment of the robotic system of FIG. 1 arranged for ureteroscopy.

FIG. 3A illustrates an embodiment of the system 100 of FIG. 1 arranged for ureteroscopy. In a ureteroscopic procedure, the cart 102 may be positioned to deliver a ureteroscope 302, a procedure-specific endoscope designed to traverse a patient's urethra and ureter, to the lower abdominal area of the patient. In ureteroscopy, it may be desirable for the ureteroscope 302 to be directly aligned with the patient's urethra to reduce friction and forces on the sensitive anatomy. As shown, the cart 102 may be aligned at the foot of the table to allow the robotic arms 104 to position the ureteroscope 302 for direct linear access to the patient's urethra. From the foot of the table, the robotic arms 104 may insert the ureteroscope 302 along a virtual rail 304 directly into the patient's lower abdomen through the urethra.

After insertion into the urethra, using similar control techniques as in bronchoscopy, the ureteroscope 302 may be navigated into the bladder, ureters, and/or kidneys for diagnostic and/or therapeutic applications. For example, the ureteroscope 302 may be directed into the ureter and kidneys to break up kidney stone build-up using a laser or ultrasonic lithotripsy device deployed down a working channel of the ureteroscope 302. After lithotripsy is complete, the resulting stone fragments may be removed using baskets deployed down the working channel of the ureteroscope 302.

Figure 3B:
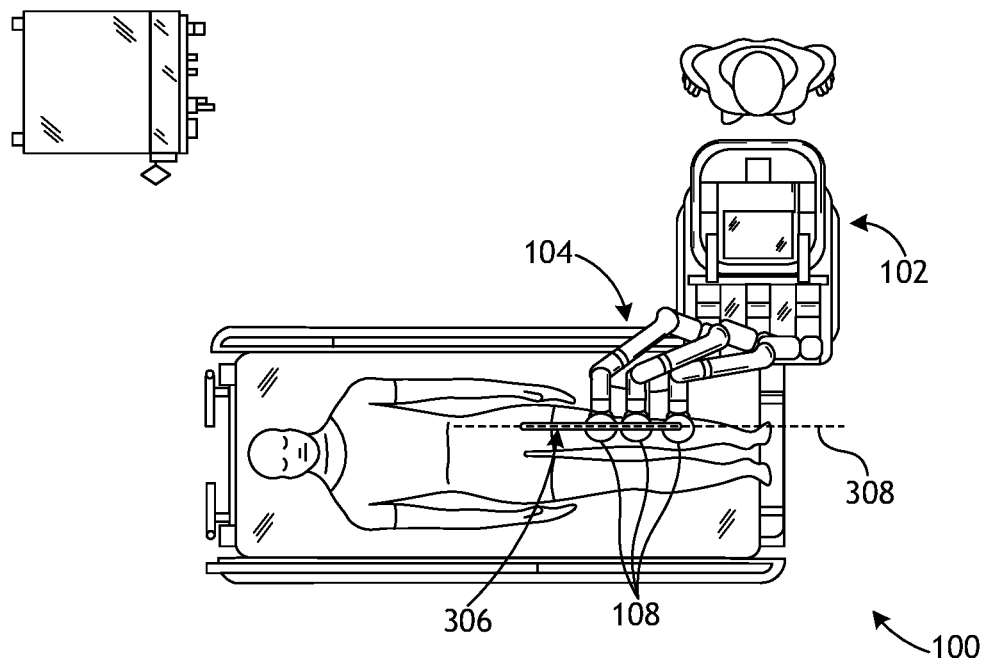
FIG. 3B illustrates an embodiment of the robotic system of FIG. 1 arranged for a vascular procedure.

FIG. 3B illustrates another embodiment of the system 100 of FIG. 1 arranged for a vascular procedure. In a vascular procedure, the system 100 may be configured such that the cart 102 may deliver a medical instrument 306, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 102 may be positioned towards the patient's legs and lower abdomen to allow the robotic arms 104 to provide a virtual rail 308 with direct linear access to the femoral artery access point in the patient's thigh/hip region. After insertion into the artery, the medical instrument 306 may be directed and advanced by translating the instrument drivers 108. Alternatively, the cart 102 may be positioned around the patient's upper abdomen in order to reach alternative vascular access points, such as, for example, the carotid and brachial arteries near the patient's shoulder and wrist.

B. Robotic System—Table.

Figure 4:
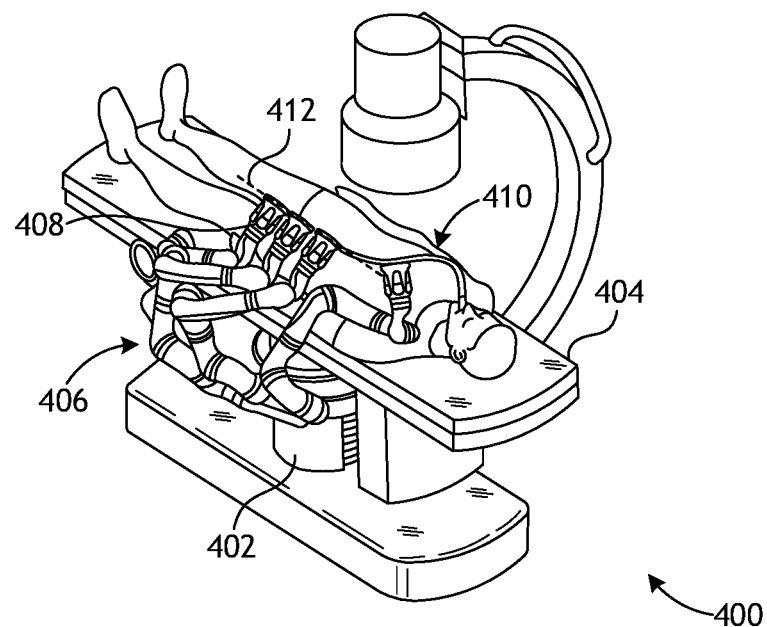
FIG. 4 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 4 illustrates an embodiment of such a robotically-enabled system 400 arranged for a bronchoscopy procedure. As illustrated, the system 400 includes a support structure or column 402 for supporting platform 404 (shown as a "table" or "bed") over the floor. Much like in the cart-based systems, the end effectors of the robotic arms 406 of the system 400 comprise instrument drivers 408 that are designed to manipulate an elongated medical instrument, such as a bronchoscope 410, through or along a virtual rail 412 formed from the linear alignment of the instrument drivers 408. In practice, a C-arm for providing fluoroscopic imaging may be positioned over the patient's upper abdominal area by placing the emitter and detector around the table 404.

Figure 5:
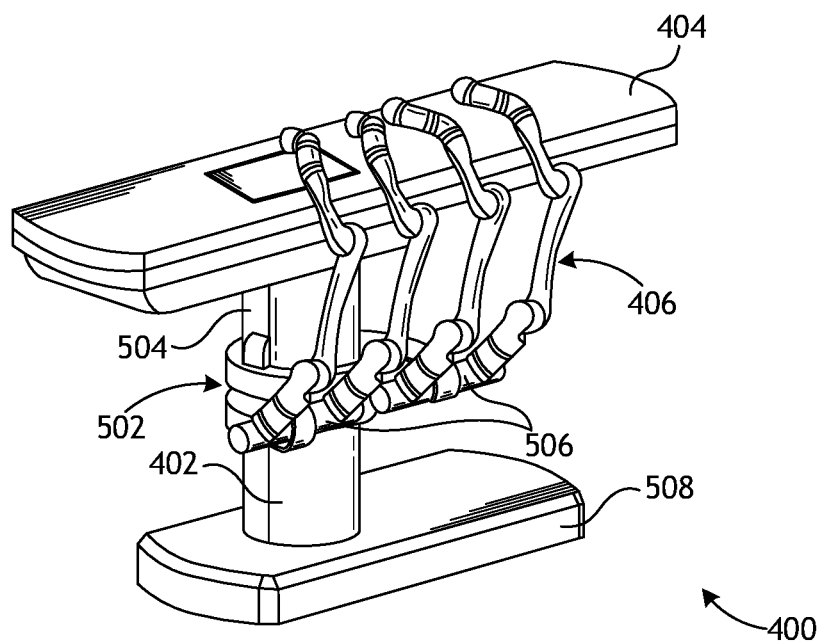
FIG. 5 provides an alternative view of the robotic system of FIG. 4.

FIG. 5 provides an alternative view of the system 400 without the patient and medical instrument for discussion purposes. As shown, the column 402 may include one or more carriages 502 shown as ring-shaped in the system 400, from which the one or more robotic arms 406 may be based. The carriages 502 may translate along a vertical column interface 504 that runs the length (height) of the column 402 to provide different vantage points from which the robotic arms 406 may be positioned to reach the patient. The carriage(s) 502 may rotate around the column 402 using a mechanical motor positioned within the column 402 to allow the robotic arms 406 to have access to multiples sides of the table 404, such as, for example, both sides of the patient. In embodiments with multiple carriages 502, the carriages 502 may be individually positioned on the column 402 and may translate and/or rotate independent of the other carriages 502. While carriages 502 need not surround the column 402 or even be circular, the ring-shape as shown facilitates rotation of the carriages 502 around the column 402 while maintaining structural balance. Rotation and translation of the carriages 502 allows the system 400 to align medical instruments, such as endoscopes and laparoscopes, into different access points on the patient.

In other embodiments (discussed in greater detail below with respect to FIG. 9A), the system 400 can include a patient table or bed with adjustable arm supports in the form of bars or rails extending alongside it. One or more robotic arms 406 (e.g., via a shoulder with an elbow joint) can be attached to the adjustable arm supports, which can be vertically adjusted. By providing vertical adjustment, the robotic arms 406 are advantageously capable of being stowed compactly beneath the patient table or bed, and subsequently raised during a procedure.

The arms 406 may be mounted on the carriages 502 through a set of arm mounts 506 comprising a series of joints that may individually rotate and/or telescopically extend to provide additional configurability to the robotic arms 406. Additionally, the arm mounts 506 may be positioned on the carriages 502 such that when the carriages 502 are appropriately rotated, the arm mounts 506 may be positioned on either the same side of the table 404 (as shown in FIG. 5), on opposite sides of table 404 (as shown in FIG. 7B), or on adjacent sides of the table 404 (not shown).

The column 402 structurally provides support for the table 404, and a path for vertical translation of the carriages 502. Internally, the column 402 may be equipped with lead screws for guiding vertical translation of the carriages, and motors to mechanize the translation of said carriages based the lead screws. The column 402 may also convey power and control signals to the carriage 502 and robotic arms 406 mounted thereon.

A table base 508 serves a similar function as the cart base 204 of the cart 102 shown in FIG. 2, housing heavier components to balance the table/bed 404, the column 402, the carriages 502, and the robotic arms 406. The table base 508 may also incorporate rigid casters to provide stability during procedures. Deployed from the bottom of the table base 508, the casters may extend in opposite directions on both sides of the base 508 and retract when the system 400 needs to be moved.

In some embodiments, the system 400 may also include a tower (not shown) that divides the functionality of system 400 between table and tower to reduce the form factor and bulk of the table 404. As in earlier disclosed embodiments, the tower may provide a variety of support functionalities to the table 404, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 508 for potential stowage of the robotic arms 406. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 6:
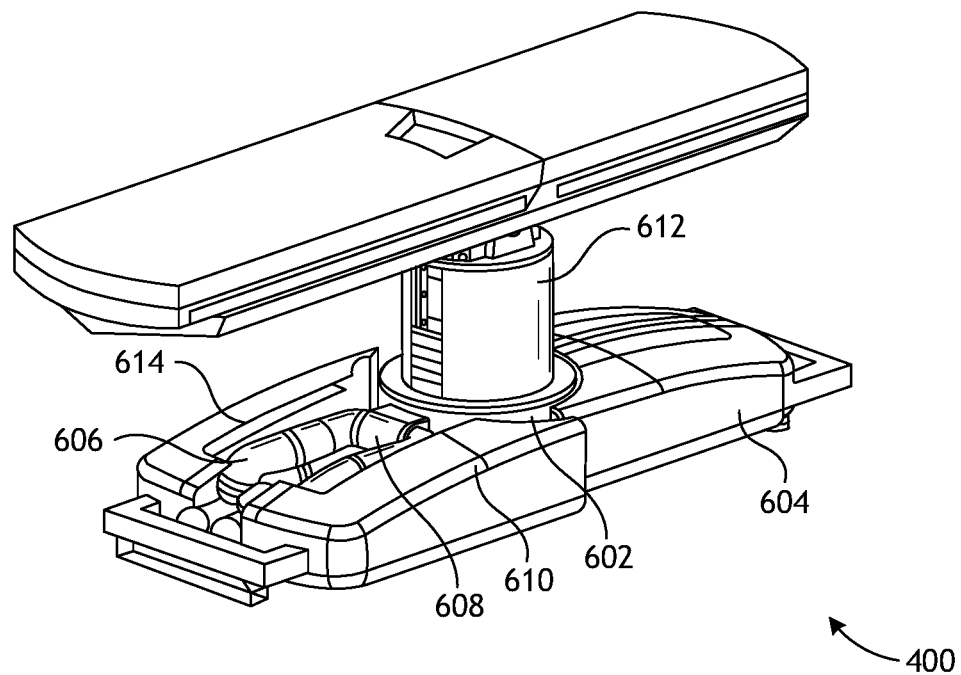
FIG. 6 illustrates an example system configured to stow robotic arm(s).

In some embodiments, a table base may stow and store the robotic arms when not in use. FIG. 6 illustrates an embodiment of the system 400 that is configured to stow robotic arms in an embodiment of the table-based system. In the system 400, one or more carriages 602 (one shown) may be vertically translated into a base 604 to stow one or more robotic arms 606, one or more arm mounts 608, and the carriages 602 within the base 604. Base covers 610 may be translated and retracted open to deploy the carriages 602, the arm mounts 608, and the arms 606 around the column 612, and closed to stow and protect them when not in use. The base covers 610 may be sealed with a membrane 614 along the edges of its opening to prevent dirt and fluid ingress when closed.

Figure 7A:
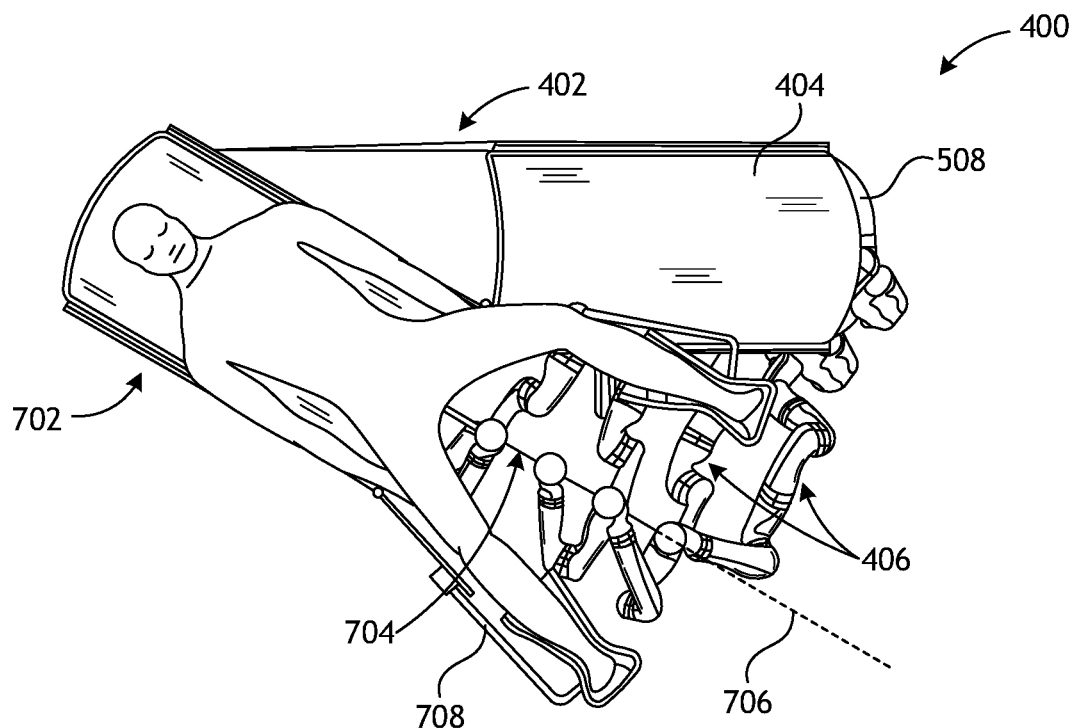
FIG. 7A illustrates an embodiment of a table-based robotic system configured for a ureteroscopy procedure.
Figure 7B:
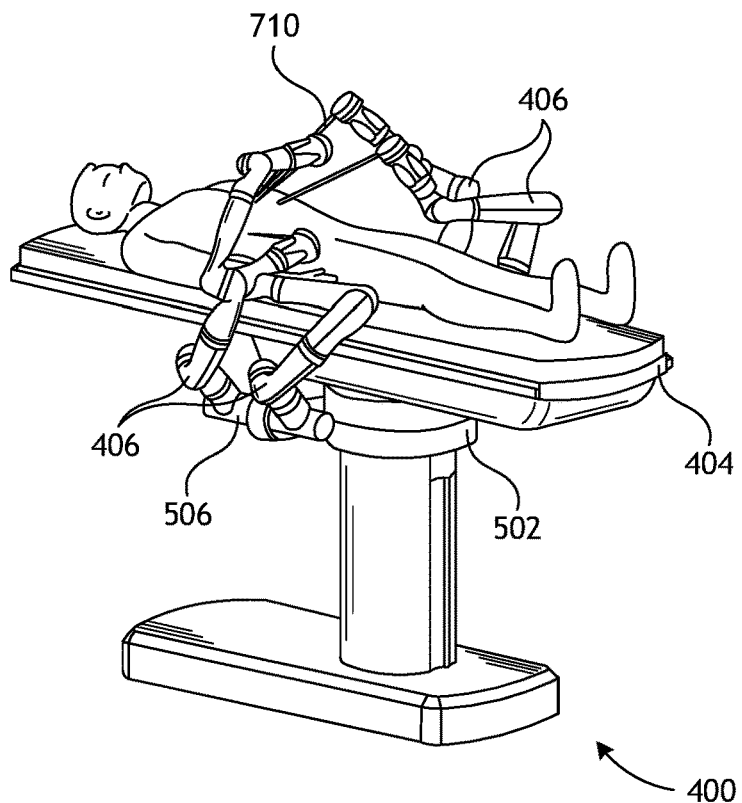
FIG. 7B illustrates an embodiment of a table-based robotic system configured for a laparoscopic procedure.

FIG. 7A illustrates an embodiment of the robotically-enabled table-based system 400 configured for a ureteroscopy procedure. In ureteroscopy, the table 404 may include a swivel portion 702 for positioning a patient off-angle from the column 402 and the table base 508. The swivel portion 702 may rotate or pivot around a pivot point (e.g., located below the patient's head) in order to position the bottom portion of the swivel portion 702 away from the column 402. For example, the pivoting of the swivel portion 702 allows a C-arm (not shown) to be positioned over the patient's lower abdomen without competing for space with the column (not shown) below table 404. By rotating the carriage (not shown) around the column 402, the robotic arms 406 may directly insert a ureteroscope 704 along a virtual rail 706 into the patient's groin area to reach the urethra. In ureteroscopy, stirrups 708 may also be fixed to the swivel portion 702 of the table 404 to support the position of the patient's legs during the procedure and allow clear access to the patient's groin area.

FIG. 7B illustrates an embodiment of the system 400 configured for a laparoscopic procedure. In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. As shown in FIG. 7B, the carriages 502 of the system 400 may be rotated and vertically adjusted to position pairs of the robotic arms 406 on opposite sides of the table 404, such that an instrument 710 may be positioned using the arm mounts 506 to be passed through minimal incisions on both sides of the patient to reach his/her abdominal cavity.

Figure 7C:
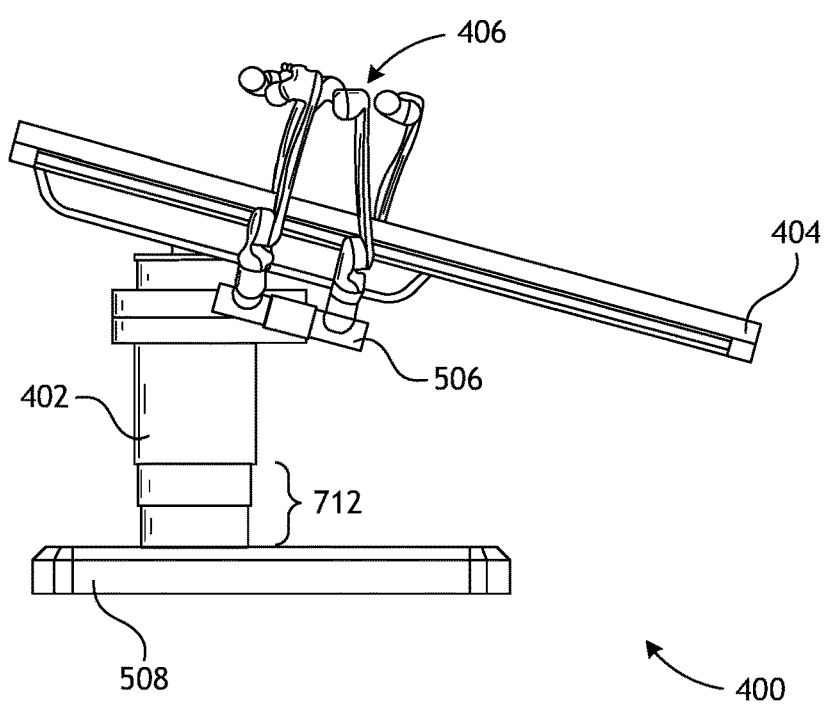
FIG. 7C illustrates an embodiment of the table-based robotic system of FIGS. 4-7B with pitch or tilt adjustment.

To accommodate laparoscopic procedures, the system 400 may also tilt the platform to a desired angle. FIG. 7C illustrates an embodiment of the system 400 with pitch or tilt adjustment. As shown in FIG. 7C, the system 400 may accommodate tilt of the table 404 to position one portion of the table 404 at a greater distance from the floor than the other. Additionally, the arm mounts 506 may rotate to match the tilt such that the arms 406 maintain the same planar relationship with table 404. To accommodate steeper angles, the column 402 may also include telescoping portions 712 that allow vertical extension of the column 402 to keep the table 404 from touching the floor or colliding with the base 508.

Figure 8:
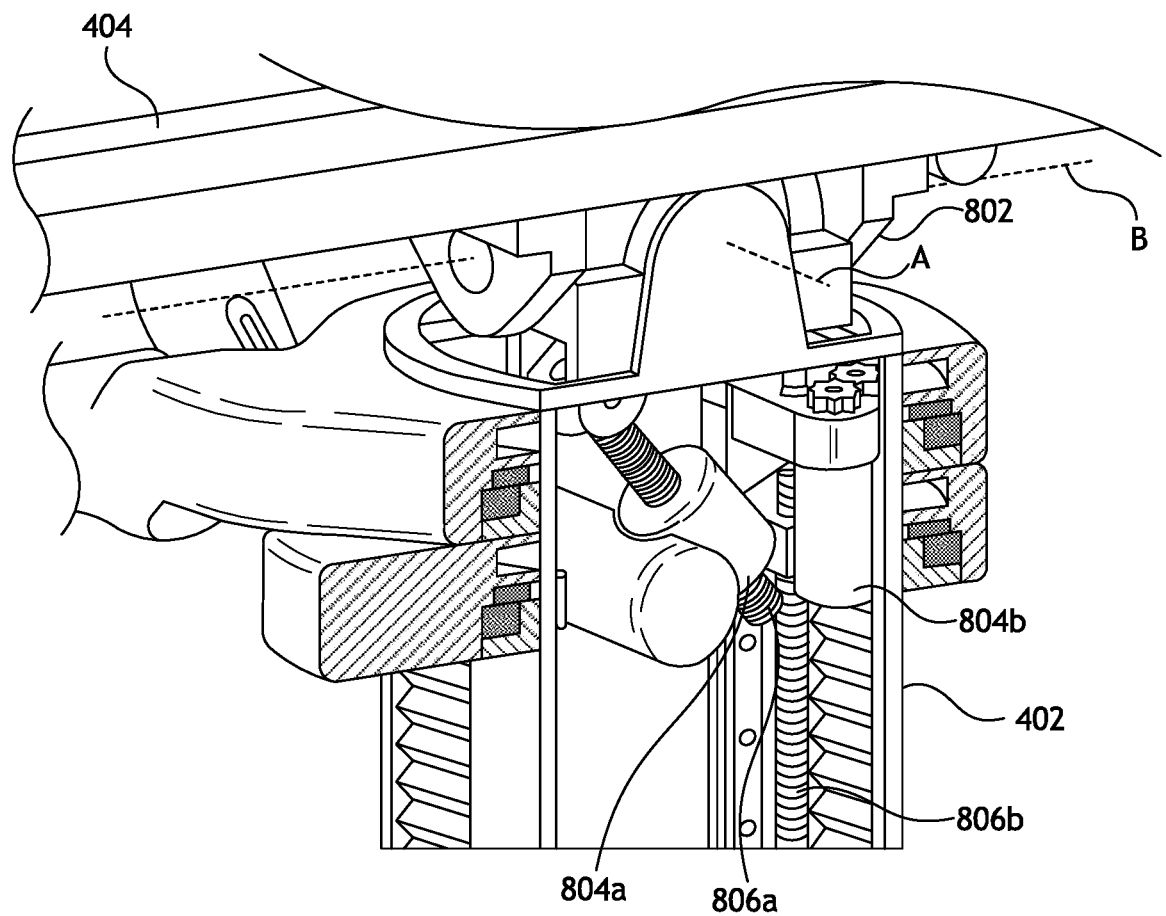
FIG. 8 provides a detailed illustration of the interface between the table and the column of the table-based robotic system of FIGS. 4-7.

FIG. 8 provides a detailed illustration of the interface between the table 404 and the column 402. Pitch rotation mechanism 802 may be configured to alter the pitch angle of the table 404 relative to the column 402 in multiple degrees of freedom. The pitch rotation mechanism 802 may be enabled by the positioning of orthogonal axes A and B at the column-table interface, each axis actuated by a separate motor 804a and 804b responsive to an electrical pitch angle command. Rotation along one screw 806a would enable tilt adjustments in one axis A, while rotation along another screw 806b would enable tilt adjustments along the other axis B. In some embodiments, a ball joint can be used to alter the pitch angle of the table 404 relative to the column 402 in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 9A:
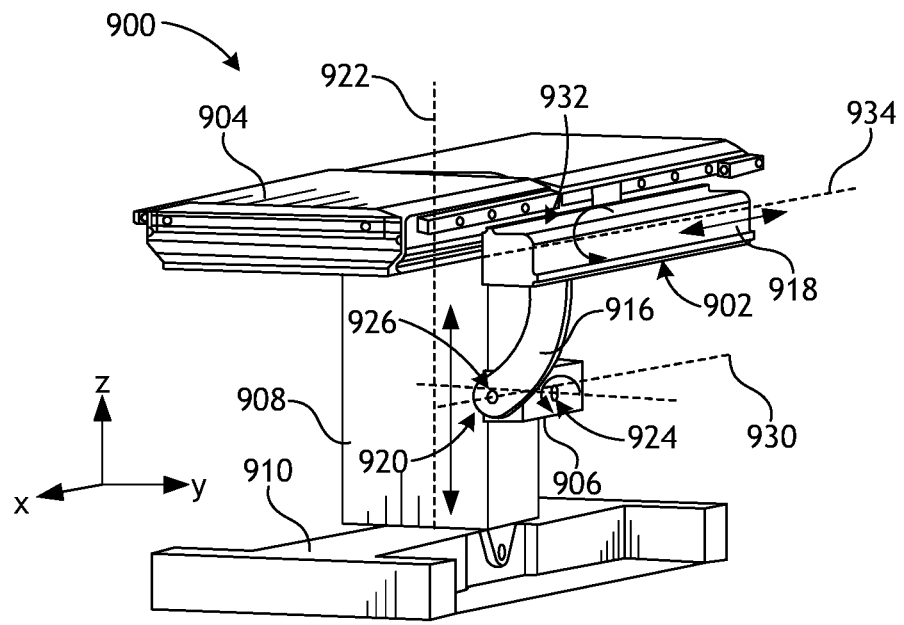
FIG. 9A illustrates an alternative embodiment of a table-based robotic system.
Figure 9B:
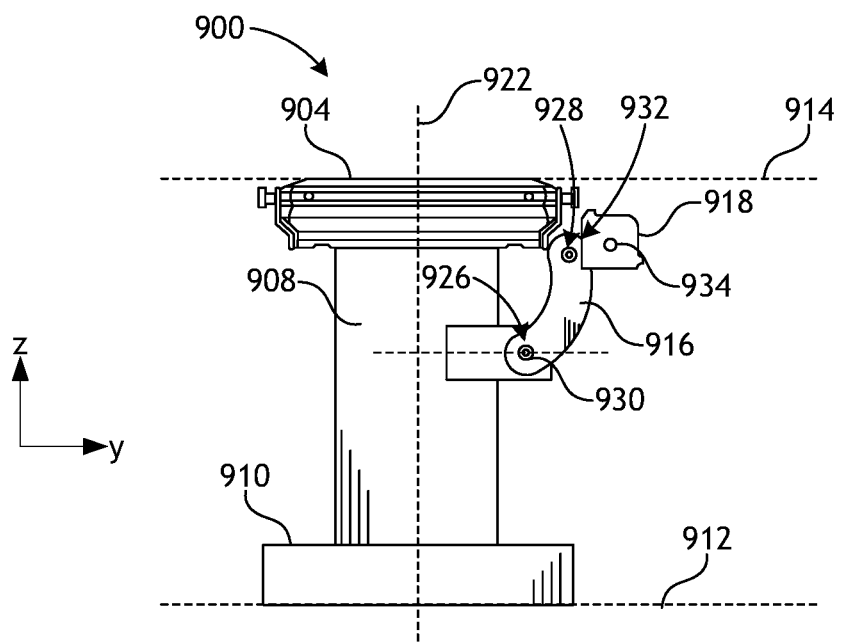
FIG. 9B illustrates an end view of the table-based robotic system of FIG. 9A.

FIGS. 9A and 9B illustrate isometric and end views, respectively, of an alternative embodiment of a table-based surgical robotics system 900. The surgical robotics system 900 includes one or more adjustable arm supports 902 that can be configured to support one or more robotic arms (see, for example, FIG. 9C) relative to a table 904. In the illustrated embodiment, a single adjustable arm support 902 is shown, though an additional arm support can be provided on an opposite side of the table 904. The adjustable arm support 902 can be configured so that it can move relative to the table 904 to adjust and/or vary the position of the adjustable arm support 902 and/or any robotic arms mounted thereto relative to the table 904. For example, the adjustable arm support 902 may be adjusted in one or more degrees of freedom relative to the table 904. The adjustable arm support 902 provides high versatility to the system 900, including the ability to easily stow the one or more adjustable arm supports 902 and any robotics arms attached thereto beneath the table 904. The adjustable arm support 902 can be elevated from the stowed position to a position below an upper surface of the table 904. In other embodiments, the adjustable arm support 902 can be elevated from the stowed position to a position above an upper surface of the table 904.

The adjustable arm support 902 can provide several degrees of freedom, including lift, lateral translation, tilt, etc. In the illustrated embodiment of FIGS. 9A and 9B, the arm support 902 is configured with four degrees of freedom, which are illustrated with arrows in FIG. 9A. A first degree of freedom allows for adjustment of the adjustable arm support 902 in the z-direction ("Z-lift"). For example, the adjustable arm support 902 can include a carriage 906 configured to move up or down along or relative to a column 908 supporting the table 904. A second degree of freedom can allow the adjustable arm support 902 to tilt. For example, the adjustable arm support 902 can include a rotary joint, which can allow the adjustable arm support 902 to be aligned with the bed in a Trendelenburg position. A third degree of freedom can allow the adjustable arm support 902 to "pivot up," which can be used to adjust a distance between a side of the table 904 and the adjustable arm support 902. A fourth degree of freedom can permit translation of the adjustable arm support 902 along a longitudinal length of the table.

The surgical robotics system 900 in FIGS. 9A and 9B can comprise a table 904 supported by a column 908 that is mounted to a base 910. The base 910 and the column 908 support the table 904 relative to a support surface. A floor axis 912 and a support axis 914 are shown in FIG. 9B.

The adjustable arm support 902 can be mounted to the column 908. In other embodiments, the arm support 902 can be mounted to the table 904 or the base 910. The adjustable arm support 902 can include a carriage 906, a bar or rail connector 916 and a bar or rail 918. In some embodiments, one or more robotic arms mounted to the rail 918 can translate and move relative to one another.

The carriage 906 can be attached to the column 908 by a first joint 920, which allows the carriage 906 to move relative to the column 908 (e.g., such as up and down a first or vertical axis 922). The first joint 920 can provide the first degree of freedom ("Z-lift") to the adjustable arm support 902. The adjustable arm support 902 can include a second joint 924, which provides the second degree of freedom (tilt) for the adjustable arm support 902. The adjustable arm support 902 can include a third joint 926, which can provide the third degree of freedom ("pivot up") for the adjustable arm support 902. An additional joint 928 (shown in FIG. 9B) can be provided that mechanically constrains the third joint 926 to maintain an orientation of the rail 918 as the rail connector 916 is rotated about a third axis 930. The adjustable arm support 902 can include a fourth joint 932, which can provide a fourth degree of freedom (translation) for the adjustable arm support 902 along a fourth axis 934.

Figure 9C:
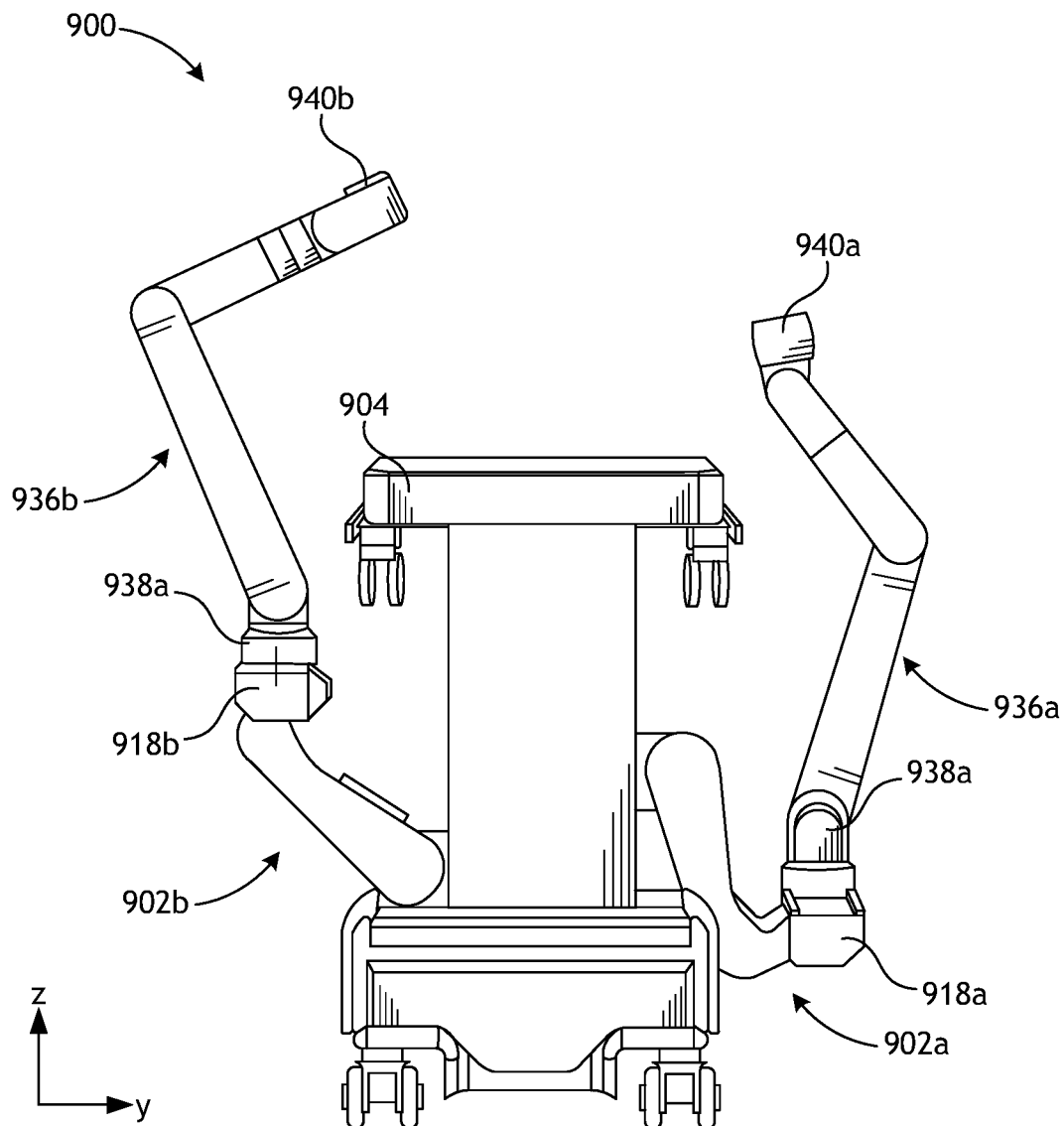
FIG. 9C illustrates an end view of a table-based robotic system with robotic arms attached thereto.

FIG. 9C illustrates an end view of the surgical robotics system 900 with two adjustable arm supports 902a and 902b mounted on opposite sides of the table 904. A first robotic arm 936a is attached to the first bar or rail 918a of the first adjustable arm support 902a. The first robotic arm 936a includes a base 938a attached to the first rail 918a. The distal end of the first robotic arm 936a includes an instrument drive mechanism or input 940a that can attach to one or more robotic medical instruments or tools. Similarly, the second robotic arm 936b includes a base 938a attached to the second rail 918b. The distal end of the second robotic arm 936b includes an instrument drive mechanism or input 940b configured to attach to one or more robotic medical instruments or tools.

In some embodiments, one or more of the robotic arms 936a,b comprises an arm with seven or more degrees of freedom. In some embodiments, one or more of the robotic arms 936a,b can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 938a,b (1-degree of freedom including translation). In some embodiments, the insertion degree of freedom can be provided by the robotic arm 936a,b, while in other embodiments, the instrument itself provides insertion via an instrument-based insertion architecture.

C. Instrument Driver & Interface.

The end effectors of a system's robotic arms comprise (i) an instrument driver (alternatively referred to as "tool driver," "instrument drive mechanism," "instrument device manipulator," and "drive input") that incorporate electro-mechanical means for actuating the medical instrument, and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 10:
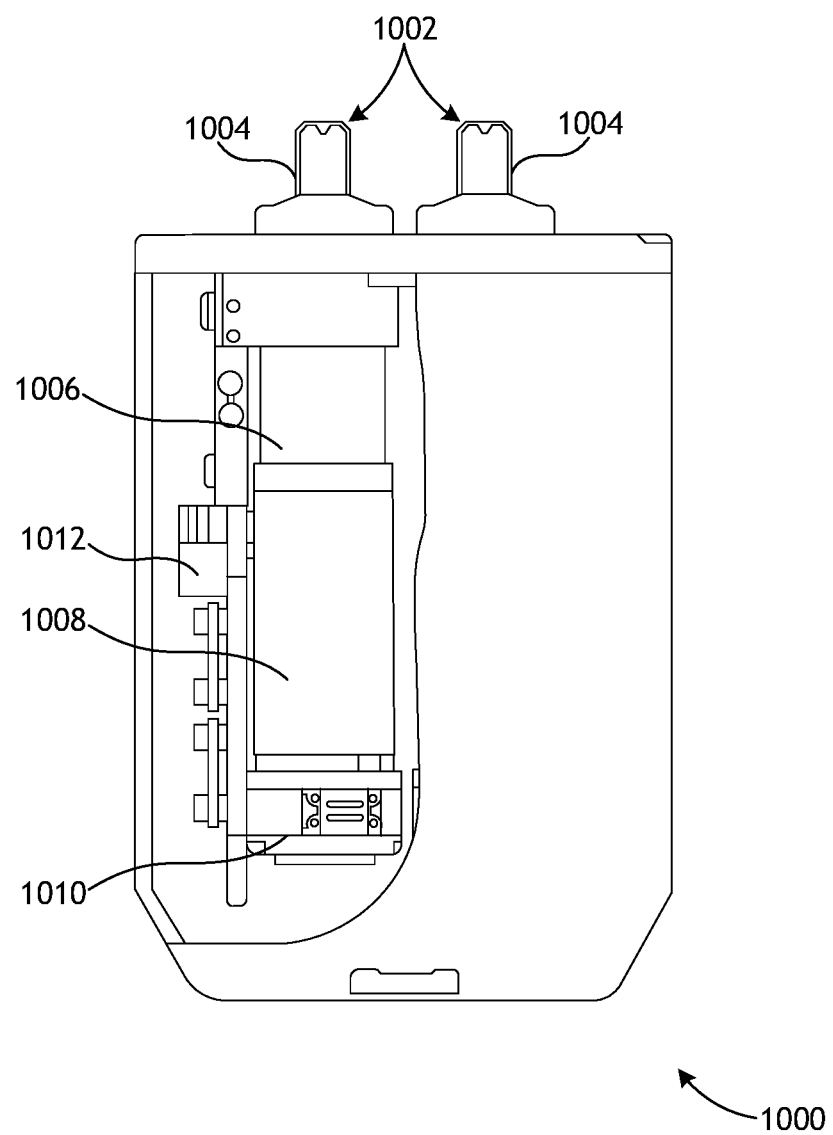
FIG. 10 illustrates an exemplary instrument driver.

FIG. 10 illustrates an example instrument driver 1000, according to one or more embodiments. Positioned at the distal end of a robotic arm, the instrument driver 1000 includes one or more drive outputs 1002 arranged with parallel axes to provide controlled torque to a medical instrument via corresponding drive shafts 1004. Each drive output 1002 comprises an individual drive shaft 1004 for interacting with the instrument, a gear head 1006 for converting the motor shaft rotation to a desired torque, a motor 1008 for generating the drive torque, and an encoder 1010 to measure the speed of the motor shaft and provide feedback to control circuitry 1012, which can also be used for receiving control signals and actuating the drive output 1002. Each drive output 1002 being independently controlled and motorized, the instrument driver 1000 may provide multiple (at least two shown in FIG. 10) independent drive outputs to the medical instrument. In operation, the control circuitry 1012 receives a control signal, transmits a motor signal to the motor 1008, compares the resulting motor speed as measured by the encoder 1010 with the desired speed, and modulates the motor signal to generate the desired torque.

For procedures that require a sterile environment, the robotic system may incorporate a drive interface, such as a sterile adapter connected to a sterile drape that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 11:
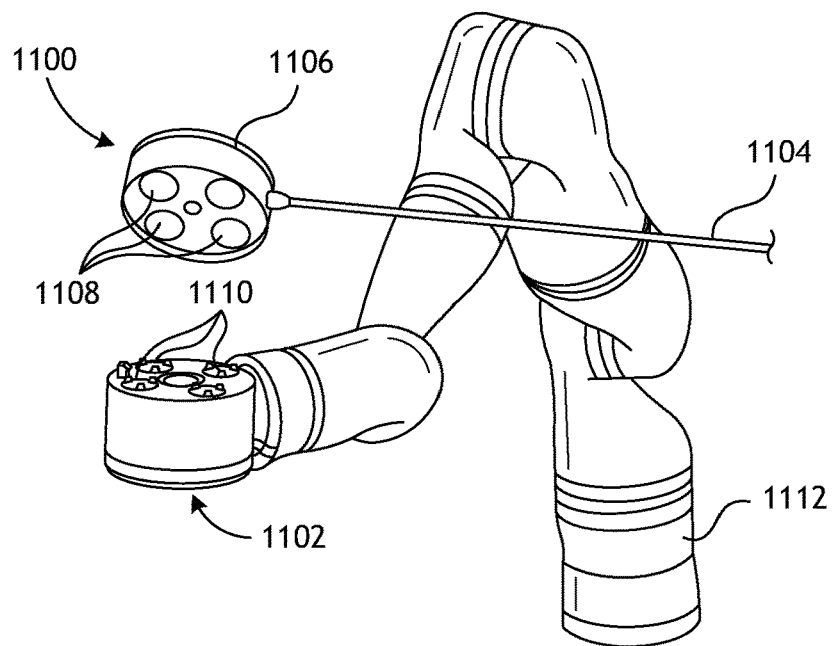
FIG. 11 illustrates an exemplary medical instrument with a paired instrument driver.

FIG. 11 illustrates an example medical instrument 1100 with a paired instrument driver 1102. Like other instruments designed for use with a robotic system, the medical instrument 1100 (alternately referred to as a "surgical tool") comprises an elongated shaft 1104 (or elongate body) and an instrument base 1106. The instrument base 1106, also referred to as an "instrument handle" due to its intended design for manual interaction by the physician, may generally comprise rotatable drive inputs 1108, e.g., receptacles, pulleys or spools, that are designed to be mated with drive outputs 1110 that extend through a drive interface on the instrument driver 1102 at the distal end of a robotic arm 1112. When physically connected, latched, and/or coupled, the mated drive inputs 1108 of the instrument base 1106 may share axes of rotation with the drive outputs 1110 in the instrument driver 1102 to allow the transfer of torque from the drive outputs 1110 to the drive inputs 1108. In some embodiments, the drive outputs 1110 may comprise splines that are designed to mate with receptacles on the drive inputs 1108.

The elongated shaft 1104 is designed to be delivered through either an anatomical opening or lumen, e.g., as in endoscopy, or a minimally invasive incision, e.g., as in laparoscopy. The elongated shaft 1104 may be either flexible (e.g., having properties similar to an endoscope) or rigid (e.g., having properties similar to a laparoscope) or contain a customized combination of both flexible and rigid portions. When designed for laparoscopy, the distal end of the shaft 1104 may be connected to an end effector extending from a jointed wrist formed from a clevis with at least one degree of freedom and a surgical tool or medical instrument, such as, for example, a grasper or scissors, that may be actuated based on force from the tendons as the drive inputs 1008 rotate in response to torque received from the drive outputs 1110 of the instrument driver 1102. When designed for endoscopy, the distal end of the flexible elongated shaft 1104 may include a steerable or controllable bending section that may be articulated and bent based on torque received from the drive outputs 1110 of the instrument driver 1102.

In some embodiments, torque from the instrument driver 1102 is transmitted down the elongated shaft 1104 using tendons along the shaft 1104. These individual tendons, such as pull wires, may be individually anchored to individual drive inputs 1108 within the instrument handle 1106. From the handle 1106, the tendons are directed down one or more pull lumens along the elongated shaft 1104 and anchored at the distal portion of the elongated shaft 1104, or in the wrist at the distal portion of the elongated shaft. During a surgical procedure, such as a laparoscopic, endoscopic, or a hybrid procedure, these tendons may be coupled to a distally mounted end effector, such as a wrist, a grasper, or scissors. Under such an arrangement, torque exerted on the drive inputs 1108 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 1104, where tension from the tendon cause the grasper to close.

In endoscopy, the tendons may be coupled to a bending or articulating section positioned along the elongated shaft 1104 (e.g., at the distal end) via adhesive, control ring, or other mechanical fixation. When fixedly attached to the distal end of a bending section, torque exerted on drive inputs 1108 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 1104 to allow for controlled articulation in the desired bending or articulable sections.

In endoscopy, the elongated shaft 1104 houses a number of components to assist with the robotic procedure. The shaft may comprise a working channel for deploying surgical tools (or medical instruments), irrigation, and/or aspiration to the operative region at the distal end of the shaft 1104. The shaft 1104 may also accommodate wires and/or optical fibers to transfer signals to/from an optical assembly at the distal tip, which may include of an optical camera. The shaft 1104 may also accommodate optical fibers to carry light from proximally-located light sources, such as light emitting diodes, to the distal end of the shaft.

At the distal end of the instrument 1100, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 11, the drive shaft axes, and thus the drive input axes, are orthogonal to the axis of the elongated shaft. This arrangement, however, complicates roll capabilities for the elongated shaft 1104. Rolling the elongated shaft 1104 along its axis while keeping the drive inputs 1108 static results in undesirable tangling of the tendons as they extend off the drive inputs 1108 and enter pull lumens within the elongated shaft 1104. The resulting entanglement of such tendons may disrupt any control algorithms intended to predict movement of the flexible elongated shaft during an endoscopic procedure.

Figure 12:
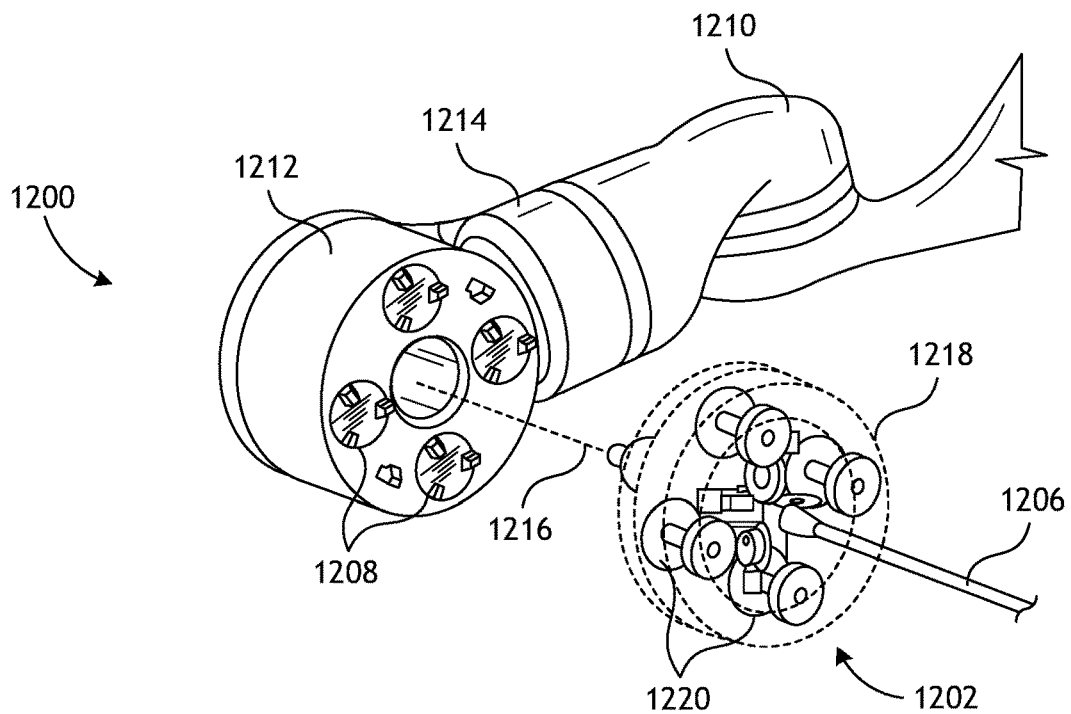
FIG. 12 illustrates an alternative design for an instrument driver and instrument where the axes of the drive units are parallel to the axis of the elongated shaft of the instrument.

FIG. 12 illustrates an alternative design for a circular instrument driver 1200 and corresponding instrument 1202 (alternately referred to as a "surgical tool") where the axes of the drive units are parallel to the axis of the elongated shaft 1206 of the instrument 1202. As shown, the instrument driver 1200 comprises four drive units with corresponding drive outputs 1208 aligned in parallel at the end of a robotic arm 1210. The drive units and their respective drive outputs 1208 are housed in a rotational assembly 1212 of the instrument driver 1200 that is driven by one of the drive units within the assembly 1212. In response to torque provided by the rotational drive unit, the rotational assembly 1212 rotates along a circular bearing that connects the rotational assembly 1212 to a non-rotational portion 1214 of the instrument driver 1200. Power and control signals may be communicated from the non-rotational portion 1214 of the instrument driver 1200 to the rotational assembly 1212 through electrical contacts maintained through rotation by a brushed slip ring connection (not shown). In other embodiments, the rotational assembly 1212 may be responsive to a separate drive unit that is integrated into the non-rotatable portion 1214, and thus not in parallel with the other drive units. The rotational assembly 1212 allows the instrument driver 1200 to rotate the drive units and their respective drive outputs 1208 as a single unit around an instrument driver axis 1216.

Like earlier disclosed embodiments, the instrument 1202 may include an elongated shaft 1206 and an instrument base 1218 (shown in phantom) including a plurality of drive inputs 1220 (such as receptacles, pulleys, and spools) that are configured to mate with the drive outputs 1208 of the instrument driver 1200. Unlike prior disclosed embodiments, the instrument shaft 1206 extends from the center of the instrument base 1218 with an axis substantially parallel to the axes of the drive inputs 1220, rather than orthogonal as in the design of FIG. 11.

When coupled to the rotational assembly 1212 of the instrument driver 1200, the medical instrument 1202, comprising instrument base 1218 and instrument shaft 1206, rotates in combination with the rotational assembly 1212 about the instrument driver axis 1216. Since the instrument shaft 1206 is positioned at the center of the instrument base 1218, the instrument shaft 1206 is coaxial with the instrument driver axis 1216 when attached. Thus, rotation of the rotational assembly 1212 causes the instrument shaft 1206 to rotate about its own longitudinal axis. Moreover, as the instrument base 1218 rotates with the instrument shaft 1206, any tendons connected to the drive inputs 1220 in the instrument base 1218 are not tangled during rotation. Accordingly, the parallelism of the axes of the drive outputs 1208, the drive inputs 1220, and the instrument shaft 1206 allows for the shaft rotation without tangling any control tendons.

Figure 13:
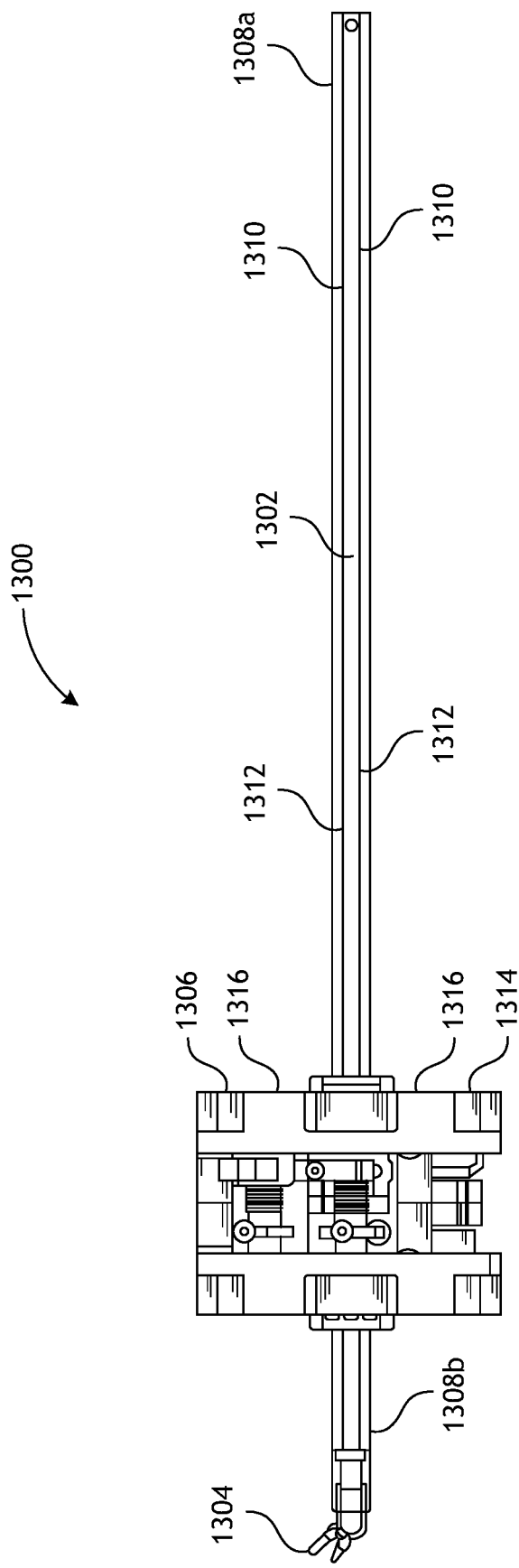
FIG. 13 illustrates an instrument having an instrument-based insertion architecture.

FIG. 13 illustrates a medical instrument 1300 having an instrument based insertion architecture in accordance with some embodiments. The instrument 1300 (alternately referred to as a "surgical tool") can be coupled to any of the instrument drivers discussed herein above and, as illustrated, can include an elongated shaft 1302, an end effector 1304 connected to the shaft 1302, and a handle 1306 coupled to the shaft 1302. The elongated shaft 1302 comprises a tubular member having a proximal portion 1308a and a distal portion 1308b. The elongated shaft 1302 comprises one or more channels or grooves 1310 along its outer surface and configured to receive one or more wires or cables 1312 therethrough. One or more cables 1312 thus run along an outer surface of the elongated shaft 1302. In other embodiments, the cables 1312 can also run through the elongated shaft 1302. Manipulation of the cables 1312 (e.g., via an instrument driver) results in actuation of the end effector 1304.

The instrument handle 1306, which may also be referred to as an instrument base, may generally comprise an attachment interface 1314 having one or more mechanical inputs 1316, e.g., receptacles, pulleys or spools, that are designed to be reciprocally mated with one or more drive outputs on an attachment surface of an instrument driver.

In some embodiments, the instrument 1300 comprises a series of pulleys or cables that enable the elongated shaft 1302 to translate relative to the handle 1306. In other words, the instrument 1300 itself comprises an instrument-based insertion architecture that accommodates insertion of the instrument 1300, thereby minimizing the reliance on a robot arm to provide insertion of the instrument 1300. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 14:
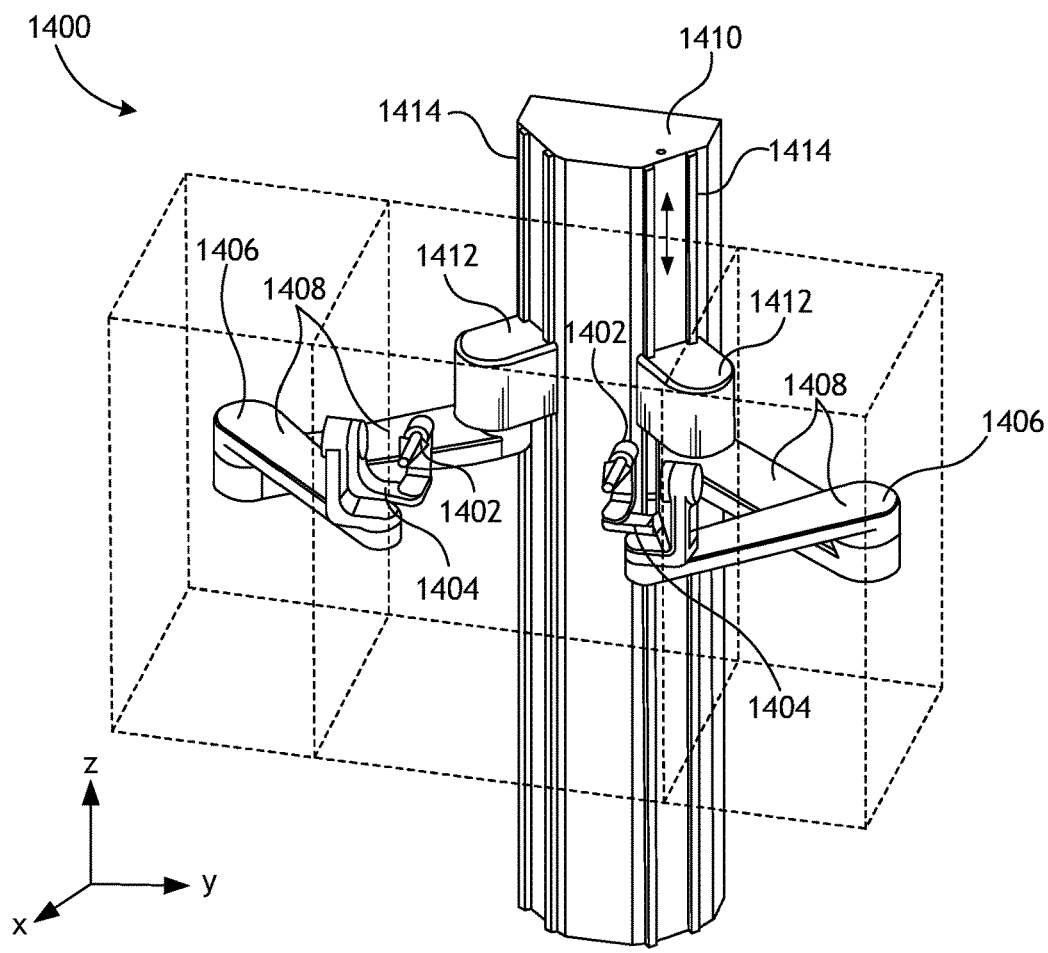
FIG. 14 illustrates an exemplary controller.

FIG. 14 is a perspective view of an embodiment of a controller 1400. In the present embodiment, the controller 1400 comprises a hybrid controller that can have both impedance and admittance control. In other embodiments, the controller 1400 can utilize just impedance or passive control. In other embodiments, the controller 1400 can utilize just admittance control. By being a hybrid controller, the controller 1400 advantageously can have a lower perceived inertia while in use.

In the illustrated embodiment, the controller 1400 is configured to allow manipulation of two medical instruments, and includes two handles 1402. Each of the handles 1402 is connected to a gimbal 1404, and each gimbal 1404 is connected to a positioning platform 1406.

As shown in FIG. 14, each positioning platform 1406 includes a selective compliance assembly robot arm (SCARA) 1408 coupled to a column 1410 by a prismatic joint 1412. The prismatic joints 1412 are configured to translate along the column 1410 (e.g., along rails 1414) to allow each of the handles 1402 to be translated in the z-direction, providing a first degree of freedom. The SCARA arm 1408 is configured to allow motion of the handle 1402 in an x-y plane, providing two additional degrees of freedom.

In some embodiments, one or more load cells are positioned in the controller 1400. For example, in some embodiments, a load cell (not shown) is positioned in the body of each of the gimbals 1404. By providing a load cell, portions of the controller 1400 are capable of operating under admittance control, thereby advantageously reducing the perceived inertia of the controller 1400 while in use. In some embodiments, the positioning platform 1406 is configured for admittance control, while the gimbal 1404 is configured for impedance control. In other embodiments, the gimbal 1404 is configured for admittance control, while the positioning platform 1406 is configured for impedance control. Accordingly, for some embodiments, the translational or positional degrees of freedom of the positioning platform 1406 can rely on admittance control, while the rotational degrees of freedom of the gimbal 1404 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 15:
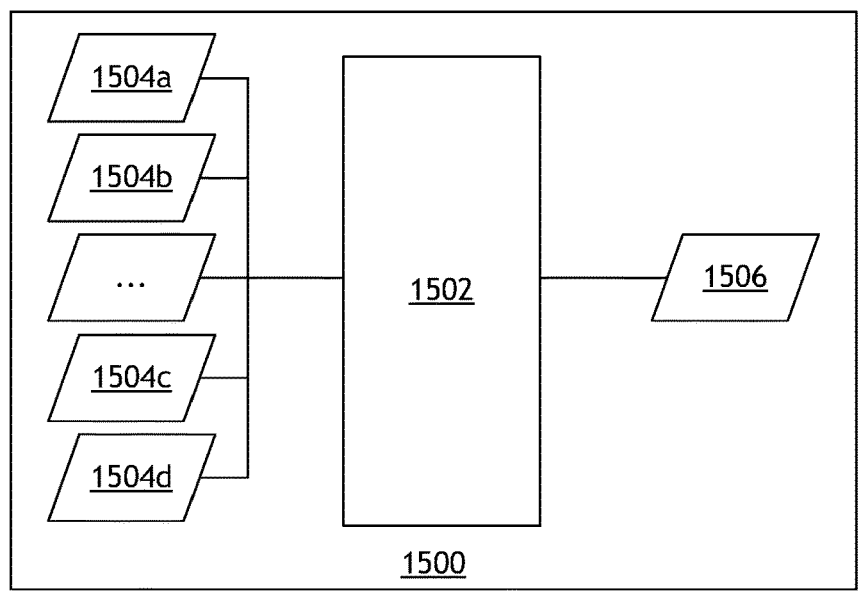
FIG. 15 depicts a block diagram illustrating a localization system that estimates a location of one or more elements of the robotic systems of FIGS. 1-7C, such as the location of the instrument of FIGS. 11-13, in accordance to an example embodiment.

FIG. 15 is a block diagram illustrating a localization system 1500 that estimates a location of one or more elements of the robotic system, such as the location of the instrument, in accordance to an example embodiment. The localization system 1500 may be a set of one or more computer devices configured to execute one or more instructions. The computer devices may be embodied by a processor (or processors) and computer-readable memory in one or more components discussed above. By way of example and not limitation, the computer devices may be in the tower 112 shown in FIG. 1, the cart 102 shown in FIGS. 1-3B, the beds shown in FIGS. 4-9, etc.

As shown in FIG. 15, the localization system 1500 may include a localization module 1502 that processes input data 1504a, 1504b, 1504c, and 1504d to generate location data 1506 for the distal tip of a medical instrument. The location data 1506 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 1504a-d are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 1504a (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 1504b. The localization module 1502 may process the vision data 1504b to enable one or more vision-based location tracking. For example, the preoperative model data may be used in conjunction with the vision data 1504b to enable computer vision-based tracking of the medical instrument (e.g., an endoscope or an instrument advance through a working channel of the endoscope). For example, using the preoperative model data 1504a, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 1502 may identify circular geometries in the preoperative model data 1504a that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 1504b to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 1502 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 1504c. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 1504d may also be used by the localization module 1502 to provide localization data 1506 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 1502. For example, although not shown in FIG. 15, an instrument utilizing shape-sensing fiber can provide shape data that the localization module 1502 can use to determine the location and shape of the instrument.

The localization module 1502 may use the input data 1504a-d in combination(s). In some cases, such a combination may use a probabilistic approach where the localization module 1502 assigns a confidence weight to the location determined from each of the input data 1504a-d. Thus, where the EM data 1504c may not be reliable (as may be the case where there is EM interference) the confidence of the location determined by the EM data 1504c can be decrease and the localization module 1502 may rely more heavily on the vision data 1504b and/or the robotic command and kinematics data 1504d.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Description.

Figure 16:
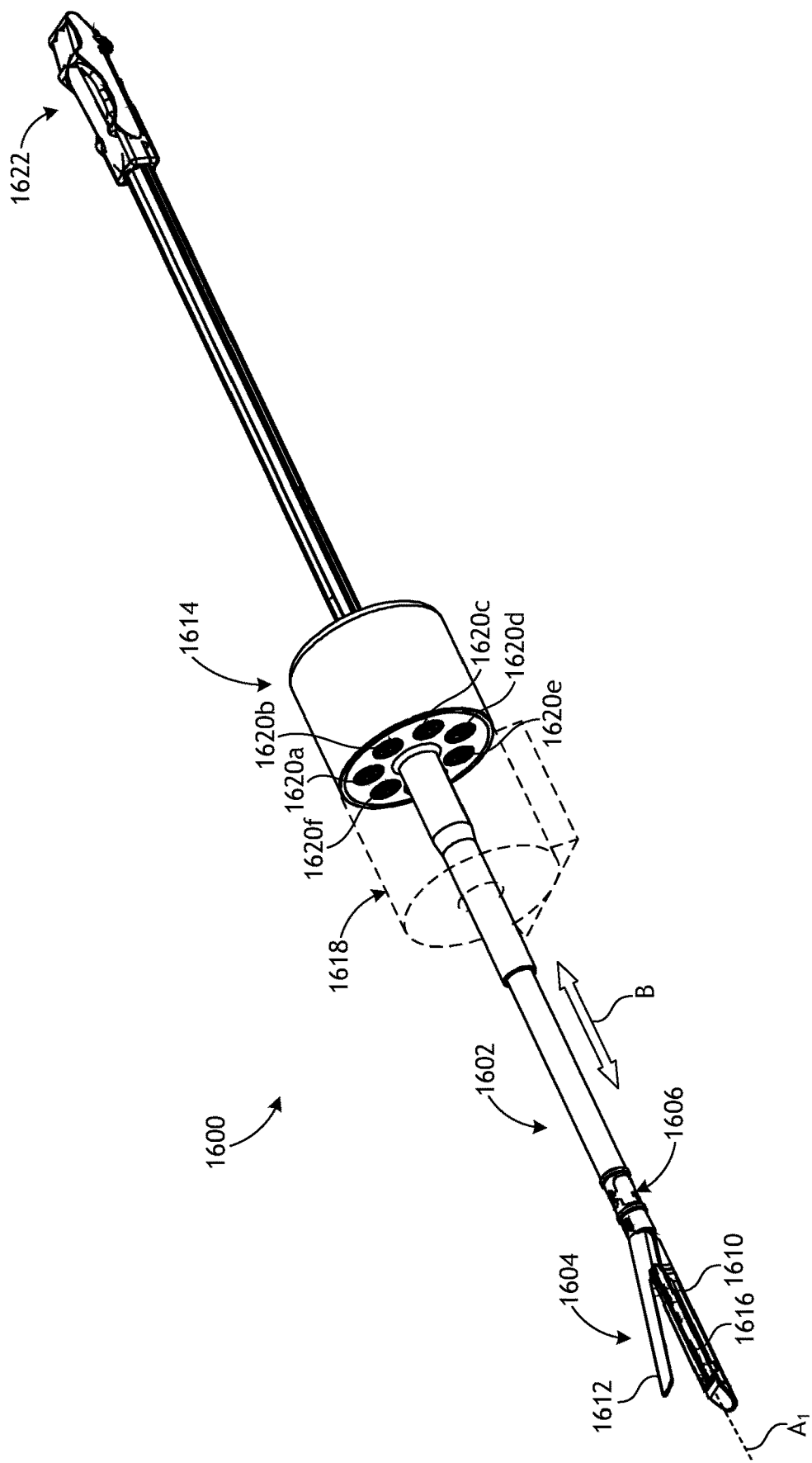
FIG. 16 is an isometric side view of an example surgical tool that may incorporate some or all of the principles of the present disclosure.

FIG. 16 is an isometric side view of an example surgical tool 1600 that may incorporate some or all of the principles of the present disclosure. The surgical tool 1600 may be similar in some respects to any of the surgical tools and medical instruments described above with reference to FIGS. 11-13 and, therefore, may be used in conjunction with a robotic surgical system, such as the robotically-enabled systems 100, 400, and 900 of FIGS. 1-9C. As illustrated, the surgical tool 1600 includes an elongated shaft 1602, an end effector 1604 arranged at the distal end of the shaft 1602, and an articulable wrist 1606 (alternately referred to as a "wrist joint") that interposes and couples the end effector 1604 to the distal end of the shaft 1602. In some embodiments, the wrist 1606 may be omitted, without departing from the scope of the disclosure.

The terms "proximal" and "distal" are defined herein relative to a robotic surgical system having an interface configured to mechanically and electrically couple the surgical tool 1600 to a robotic manipulator. The term "proximal" refers to the position of an element closer to the robotic manipulator and the term "distal" refers to the position of an element closer to the end effector 1604 and thus closer to the patient during operation. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

The surgical tool 1600 can have any of a variety of configurations capable of performing one or more surgical functions. In the illustrated embodiment, the end effector 1604 comprises a surgical stapler, alternately referred to as an "endocutter," configured to simultaneously cut and staple (fasten) tissue. As illustrated, the end effector 1604 includes opposing jaws 1610, 1612 configured to move (articulate) between open and closed positions. Alternatively, the end effector 1604 may comprise other types of instruments with opposing jaws such as, but not limited to, other types of surgical staplers (e.g., circular and linear staplers), tissue graspers, surgical scissors, advanced energy vessel sealers, clip appliers, needle drivers, a babcock including a pair of opposed grasping jaws, bipolar jaws (e.g., bipolar Maryland grasper, forceps, a fenestrated grasper, etc.), etc. In other embodiments, the end effector 1604 may instead comprise any end effector or instrument capable of being operated in conjunction with the presently disclosed robotic surgical systems and methods, such as a suction irrigator, an endoscope (e.g., a camera), or any combination thereof.

One or both of the jaws 1610, 1612 may be configured to pivot to actuate the end effector 1604 between open and closed positions. In the illustrated example, the second jaw 1612 may be rotatable (pivotable) relative to the first jaw 1610 to actuate the end effector 1604 between an open, unclamped position and a closed, clamped position. In other embodiments, however, the first jaw 1610 may move (rotate) relative to the second jaw 1612 to move the jaws 1610, 1612 between open and closed positions. In yet other embodiments, the jaws 1610, 1612 may comprise bifurcating jaws where both jaws 1610, 1612 move simultaneously between open and closed positions.

In the illustrated example, the first jaw 1610 is referred to as a "cartridge" or "channel" jaw, and the second jaw 1612 is referred to as an "anvil" jaw. The first jaw 1610 includes a frame that houses or supports a staple cartridge, and the second jaw 1612 is pivotally supported relative to the first jaw 1610 and defines a surface that operates as an anvil to deform staples ejected from the staple cartridge during operation.

The wrist 1606 enables the end effector 1604 to articulate (pivot) relative to the shaft 1602 and thereby position the end effector 1604 at various desired orientations and locations relative to a surgical site. In the illustrated embodiment, the wrist 1606 is designed to allow the end effector 1604 to pivot (swivel) left and right relative to a longitudinal axis $A_1$ of the shaft 1602. In other embodiments, however, the wrist 1606 may be designed to provide multiple degrees of freedom, including one or more translational variables (i.e., surge, heave, and sway) and/or one or more rotational variables (i.e., Euler angles or roll, pitch, and yaw). The translational and rotational variables describe the position and orientation of a component of a surgical system (e.g., the end effector 1604) with respect to a given reference Cartesian frame. "Surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The end effector 1604 is depicted in FIG. 16 in the unarticulated position where the longitudinal axis of the end effector 1604 is substantially aligned with the longitudinal axis $A_1$ of the shaft 1602, such that the end effector 1604 is at a substantially zero angle relative to the shaft 1602. In an articulated position, the longitudinal axis of the end effector 1604 would be angularly offset from the longitudinal axis $A_1$ such that the end effector 1604 would be oriented at a non-zero angle relative to the shaft 1602.

Still referring to FIG. 16, the surgical tool 1600 may also include a drive housing or "handle" 1614, and the shaft 1602 extends longitudinally through the handle 1614. The handle 1614 houses an actuation system designed to move the shaft 1602 relative to the handle 1614 in z-axis translation. Other actuation systems housed within the handle 1614 may be designed to facilitate articulation of the wrist 1606 and actuation (operation) of the end effector 1604 (e.g., clamping, firing, rotation, articulation, energy delivery, etc.). In some embodiments, the actuation systems and mechanisms housed within the handle 1614 may be actuatable to move (translate) a plurality of drive members (mostly obscured in FIG. 16) that extend along at least a portion of the shaft 1602, either on the exterior or within the interior of the shaft 1602. Example drive members include, but are not limited to, cables, bands, lines, cords, wires, woven wires, ropes, strings, twisted strings, elongate members, belts, shafts, flexible shafts, drive rods, or any combination thereof. The drive members can be made from a variety of materials including, but not limited to, a metal (e.g., tungsten, stainless steel, nitinol, etc.) a polymer (e.g., ultra-high molecular weight polyethylene, DYNEEMA®, SPECTRA®), a synthetic fiber (e.g., KEVLAR®, VECTRAN®, etc.), an elastomer, or any combination thereof.

Selective actuation of one or more of the drive members, for example, may cause the shaft 1602 to translate relative to the handle 1614, as indicated by the arrows B (i.e., z-axis translation), and thereby advance or retract the end effector 1602. Selective actuation of one or more other drive members may cause the end effector 1604 to articulate (pivot) relative to the shaft 1602 at the wrist 1606. Selective actuation of one or more additional drive members may cause the end effector 1604 to actuate (operate). Actuating the end effector 1604 depicted in FIG. 16 may entail closing and/or opening the jaws, 1610, 1612 and thereby enabling the end effector 1604 to grasp (clamp) onto tissue. Once tissue is grasped or clamped between the opposing jaws 1610, 1612, actuating the end effector 1604 may further include "firing" the end effector 1604, which may refer to causing a cutting element or knife (not visible) to advance distally within a slot or "guide track" 1616 defined in the first jaw 1610. As it moves distally, the knife transects any tissue grasped between the opposing jaws 1610, 1612, and a plurality of staples contained within the staple cartridge (e.g., housed within the first jaw 1610) are simultaneously urged (cammed) into deforming contact with corresponding anvil surfaces (e.g., pockets) provided on the second jaw 1612. The deployed staples may form multiple rows of staples that seal opposing sides of the transected tissue.

As will be appreciated, however, the end effector 1604 may be replaced with any of the other types of end effectors mentioned herein, and in those cases actuating the end effector 1604 may entail a variety of other actions or movements, without departing from the scope of the disclosure. For example, in some embodiments, the end effector 1604 may be replaced with a vessel sealer and actuating the vessel sealer may further entail triggering energy delivery (e.g., RF energy) to cauterize and/or seal tissue or vessels.

The handle 1614 provides or otherwise includes various coupling features that releasably couple the surgical tool 1600 to an instrument driver 1618 (shown in dashed lines) of a robotic surgical system. The instrument driver 1618 may be similar in some respects to the instrument drivers 1102, 1200 of FIGS. 11 and 12, respectively, and therefore may be best understood with reference thereto. Similar to the instrument drivers 1102, 1200, for example, the instrument driver 1618 may be mounted to or otherwise positioned at the end of a robotic arm (not shown) and is designed to provide the motive forces required to operate the surgical tool 1600. Unlike the instrument drivers 1102, 1200, however, the shaft 1602 of the surgical tool 1600 extends through and penetrates the instrument driver 1618.

The handle 1614 includes one or more rotatable drive inputs matable with one or more corresponding drive outputs (not shown) of the instrument driver 1618. Each drive input is actuatable to independently drive (actuate) the actuation systems and mechanisms housed within the handle 1614 and thereby operate the surgical tool 1600. In the illustrated embodiment, the handle 1614 includes a first drive input 1620a, a second drive input 1620b, a third drive input 1620c, a fourth drive input 1620d, a fifth drive input 1620e, and a sixth drive input 1620f. While six drive inputs 1620a-f are depicted, more or less than six may be included in the handle 1614 depending on the application, and without departing from the scope of the disclosure.

Each drive input 1620a-f may be matable with a corresponding drive output (not shown) of the instrument driver 1618 such that movement (rotation) of a given drive output correspondingly moves (rotates) the associated drive input 1620a-f and thereby causes various operations of the surgical tool 1600. Example operations that may be triggered by actuating the drive inputs 1620a-f include, but are not limited to, causing the knife to fire at the end effector 1604 (e.g., advancing or retracting the knife), causing the shaft 1602 to move (translate) relative to the handle 1614 along the longitudinal axis $A_1$ (i.e., z-axis translation), locking or unlocking z-axis translation of the shaft 1602, causing articulation of the end effector 1604 at the wrist 1606, and causing the jaws 1610, 1612 to open or close.

The surgical tool 1600 may further include a tailpiece 1622 arranged at a proximal end of the shaft 1602. In some embodiments, some or all of the drive members may terminate or otherwise be anchored at the tailpiece 1622.

Figure 17:
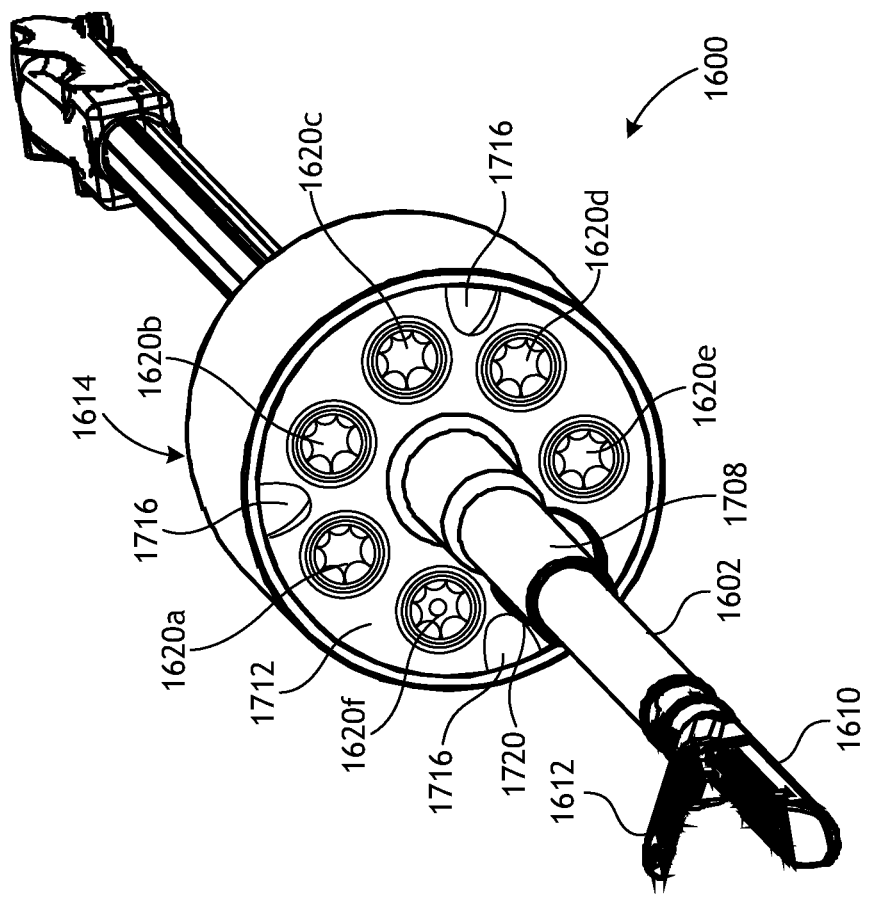
FIG. 17 depicts separated isometric end views of the instrument driver and the surgical tool of FIG. 16.
Figure 17:
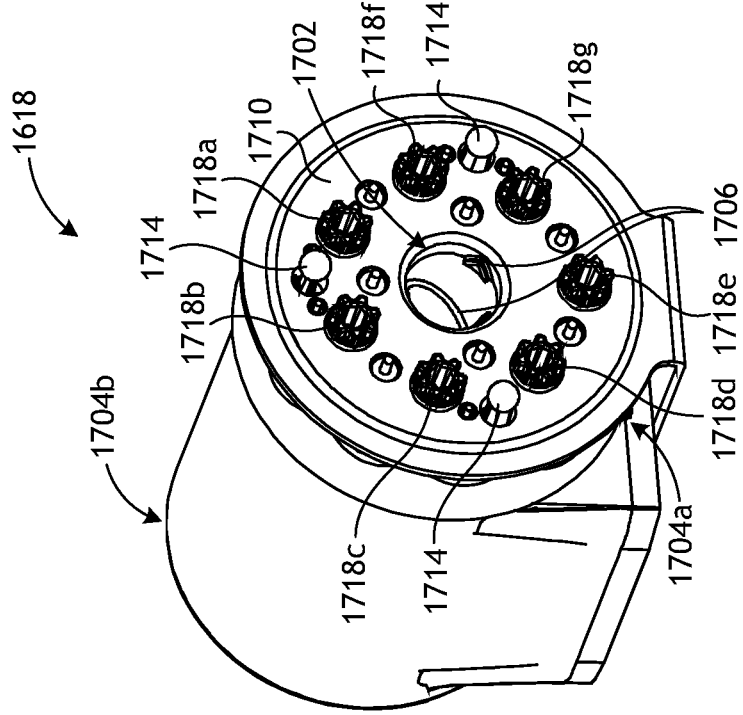

FIG. 17 depicts separated isometric end views of the instrument driver 1618 and the surgical tool 1600 of FIG. 16. With the jaws 1610, 1612 closed, the shaft 1602 and the end effector 1604 can penetrate the instrument driver 1618 by extending through a central aperture 1702 defined longitudinally through the instrument driver 1618 between first and second ends 1704a,b. In some embodiments, to align the surgical tool 1600 with the instrument driver 1618 in a proper angular orientation, one or more alignment guides 1706 may be provided or otherwise defined within the central aperture 1702 and configured to engage one or more corresponding alignment features (not shown) provided on the surgical tool 1600. The alignment feature(s) may comprise, for example, a protrusion or projection (not shown) defined on or otherwise provided by an alignment nozzle 1708 extending distally from the handle 1614. In one or more embodiments, the alignment guide(s) 1706 may comprise a curved or arcuate shoulder or lip configured to receive and guide the alignment feature as the alignment nozzle 1708 enters the central aperture 1702. As a result, the surgical tool 1600 is oriented to a proper angular alignment with the instrument driver 1618 as the alignment nozzle 1708 is advanced distally through the central aperture 1702. In other embodiments, the alignment nozzle 1708 may be omitted and the alignment feature 1712 may alternatively be provided on the shaft 1602, without departing from the scope of the disclosure.

A drive interface 1710 is provided at the first end 1704a of the instrument driver 1618 and is matable with a driven interface 1712 provided on the distal end of the handle 1614. The drive and driven interfaces 1710, 1712 may be configured to mechanically, magnetically, and/or electrically couple the handle 1614 to the instrument driver 1618. To accomplish this, in some embodiments, the drive and driven interfaces 1710, 1712 may provide one or more matable locating features configured to secure the handle 1614 to the instrument driver 1618. In the illustrated embodiment, for example, the drive interface 1710 provides one or more interlocking features 1714 (three shown) configured to locate and mate with one or more complementary-shaped pockets 1716 (two shown, one occluded) provided on the driven interface 1712. In some embodiments, the features 1714 may be configured to align and mate with the pockets 1716 via an interference or snap fit engagement, for example.

The instrument driver 1618 also includes one or more drive outputs that extend through the drive interface 1710 to mate with corresponding drive inputs 1620a-f provided at the distal end of the handle 1614. More specifically, the instrument driver 1618 includes a first drive output 1718*a* matable with the first drive input 1620*a*, a second drive output 1718*b* matable with the second drive input 1620*b*, a third drive output 1718*b* matable with the third drive input 1620*c*, a fourth drive output 1718*d* matable with the fourth drive input 1620*d*, a fifth drive output 1718*e* matable with the fifth drive input 1620*e*, and a sixth drive output 1718*f* matable with the sixth drive input 1620*f*. In some embodiments, as illustrated, the drive outputs 1718*a-f* may define splines or features designed to mate with corresponding splined receptacles of the drive inputs 1620*a-f*. Once properly mated, the drive inputs 1620*a-f* will share axes of rotation with the corresponding drive outputs 1718*a-f* to allow the transfer of rotational torque from the drive outputs 1718*a-f* to the corresponding drive inputs 1620*a-f*. In some embodiments, each drive output 1718*a-f* may be spring loaded and otherwise biased to spring outwards away from the drive interface 1710. Each drive output 1718*a-f* may be capable of partially or fully retracting into the drive interface 1710.

In some embodiments, the instrument driver 1618 may include additional drive outputs, depicted in FIG. 17B as a seventh drive output 1718*g*. The seventh drive output 1718*g* may be configured to mate with additional drive inputs (not shown) of the handle 1614 to help undertake one or more additional functions of the surgical tool 1600. In the illustrated embodiment, however, the handle 1614 does not include additional drive inputs matable with the seventh drive output 1718*g*. Instead, the driven interface 1712 defines a corresponding recess 1720 (partially occluded) configured to receive the seventh drive output 1718*g*. In other applications, however, a seventh drive input (not shown) could be included in the handle 1614 to mate with the seventh drive output 1718*g*, or the surgical tool 1600 might be replaced with another surgical tool having a seventh drive input, which would be driven by the seventh drive output 1718*g*.

While not shown, in some embodiments, an instrument sterile adapter (ISA) may be placed at the interface between the instrument driver 1618 and the handle 1614. In such applications, the interlocking features 1714 may operate as alignment features and possible latches for the ISA to be placed, stabilized, and secured. Stability of the ISA may be accomplished by a nose cone feature provided by the ISA and extending into the central aperture 1702 of the instrument driver 1618. Latching can occur either with the interlocking features 1714 or at other locations at the interface. In some cases, the ISA will provide the means to help align and facilitate the latching of the surgical tool 1600 to the ISA and simultaneously to the instrument driver 1618.

Figure 18:
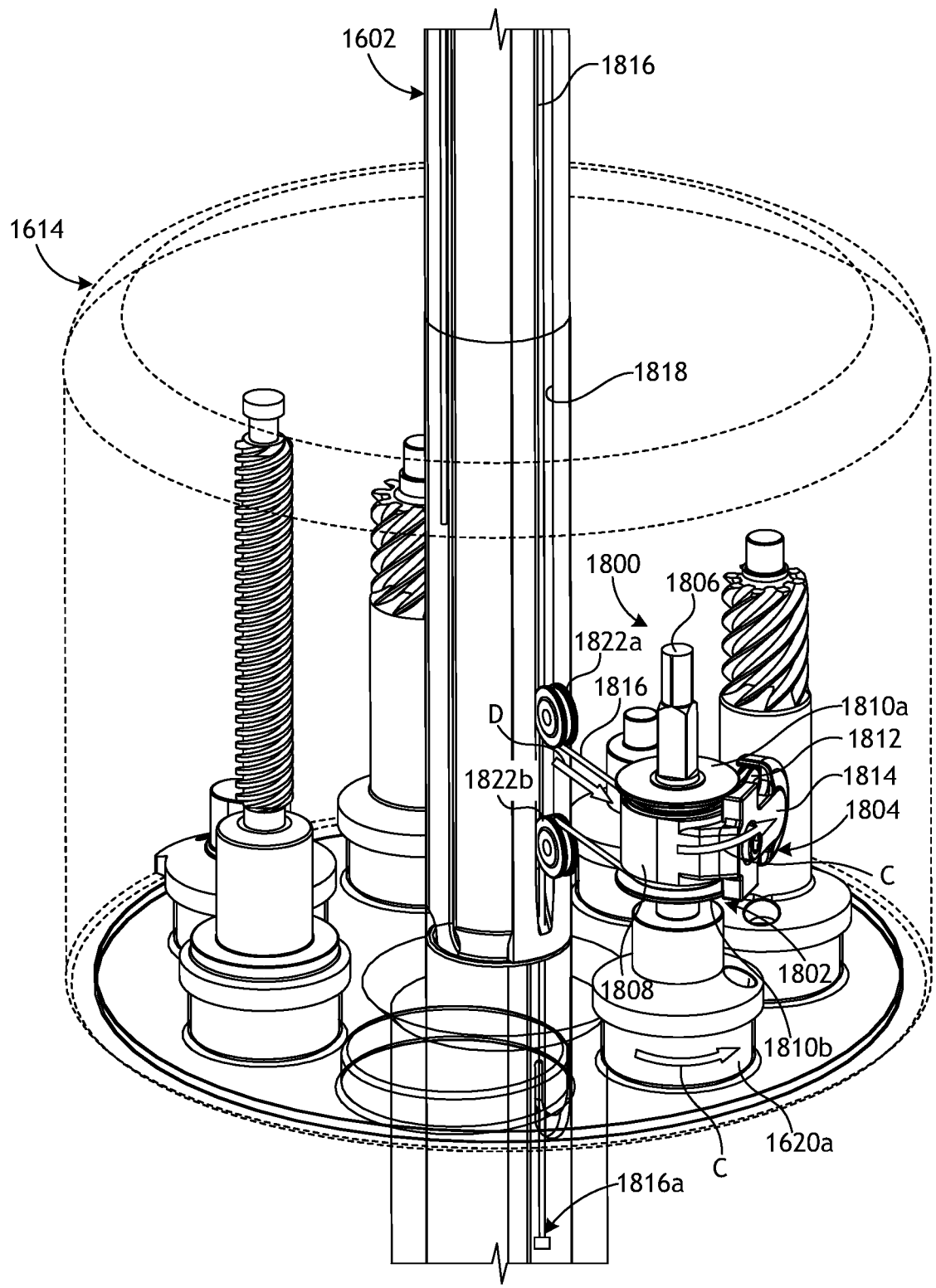
FIG. 18 is an enlarged isometric view of the handle of FIG. 16 depicting an example actuation system, according to one or more embodiments.

FIG. 18 is an enlarged isometric view of the handle 1614 of FIGS. 16-17 and depicting an example actuation system 1800, according to one or more embodiments. The outer body of the handle 1614 is shown in phantom to enable viewing of the internal mechanisms and components housed within the handle 1614, including the actuation system 1800. Various other actuation systems and component parts of the handle 1614 are omitted in FIG. 18 for simplicity.

The depicted actuation system 1800 may alternately be referred to as an "accumulator system" or a "cable differential system". In the illustrated embodiment, the actuation system 1800 is operatively coupled to the first drive input 1620*a*, but could alternatively be operatively coupled to any of the drive inputs 1620*a-f* (FIGS. 16-17), without departing from the scope of the disclosure. According to one or more embodiments, the actuation system 1800 may be operable (actuatable) to open and close the jaws 1610, 1612 (FIGS. 16-17) at the end effector 1604 (FIG. 16). In such embodiments, depending on the rotational direction of the first drive input 1620*a*, via operation of the first drive output 1718*a* (FIG. 17), the jaws 1610, 1612 may be actuated to open or close. In other embodiments, however, the actuation system 1800 may be designed to carry out other functions (operations) of the surgical tool 1600 (FIG. 16) or the end effector 1604, such as causing the shaft 1602 to translate relative to the handle 1614, causing the end effector 1604 to articulate, or causing the end effector 1604 to "fire," without departing from the scope of this disclosure.

The actuation system 1800 includes an input stack 1802 coupled to or extending from the first drive input 1620*a*. As illustrated, the input stack 1802 includes an accumulator 1804 coupled to a drive shaft 1806 extending from the first drive input 1620*a*. The drive shaft 1806 may be coupled to or form part of the first drive input 1620*a* such that rotation of the first drive input 1620*a* correspondingly rotates the drive shaft 1806 and simultaneously rotates the accumulator 1804 in the same angular direction. In at least one embodiment, the first drive input 1620*a* may form an integral part of the input stack 1802.

The accumulator 1804 may include a differential body 1808 coupled to or forming part of the drive shaft 1806, and the differential body 1808 may interpose a first or "upper" winding pulley 1810*a* and a second or "lower" winding pulley 1810*b*. In the illustrated embodiment, the upper and lower winding pulleys 1810*a,b* may be rotatably mounted to the drive shaft 1806 with corresponding bearings (not shown) and axially offset from each other, thus sharing the same axis of rotation. As described in more detail below, however, the winding pulleys 1810*a,b* may alternatively be coupled to the drive shaft 1806 without bearings. The accumulator 1804 may further include a third or "accumulator" pulley 1812 laterally offset from the upper and lower winding pulleys 1810*a,b*. In some cases, for example, the accumulator pulley 1812 may be rotatably mounted to a lateral arm 1814 extending from the differential body 1808.

The actuation system 1800 may further include a drive member 1816 that extends longitudinally along at least a portion of the shaft 1602. In the illustrated embodiment, the drive member 1816 comprises a cable or wire and, therefore, will be referred to herein as "the drive cable 1816". In other embodiments, however, the drive cable 1816 may comprise any of the other types of drive members mentioned herein. As illustrated, the drive cable 1816 may be received and extend within a groove 1818 defined in the shaft 1602. In other embodiments, however, the drive cable 1816 may alternatively be received within the interior of the shaft 1602 or extend along an exterior surface of the shaft 1602, without departing from the scope of the disclosure.

A first or "distal" end 1820*a* of the drive cable 1816 may be anchored to the shaft 1602 below (distal to) the handle 1614, and a second or "proximal" end (not shown) of the drive cable 1816 may be anchored to the shaft 1602 above (proximal to) the handle 1614. In some embodiments, a proximal end of the drive cable 1816 may be anchored at or near a proximal end of the shaft 1602, such as at the tailpiece 1622 (FIG. 16).

As illustrated, the drive cable 1816 may also extend or be threaded (guided) through the accumulator 1804 within the body of the handle 1614. To accomplish this, the actuation system 1800 may further include a first or "upper" idler pulley 1822*a* and a second or "lower" idler pulley 1822*b*. The upper and lower idler pulleys 1822*a,b* may each be rotatably coupled to the handle 1614. The upper idler pulley 1822*a* may be arranged and otherwise configured to redirect the drive cable 1816 between the shaft 1602 and the upper winding pulley 1810a, and the lower idler pulley 1822b may be arranged and otherwise configured to redirect the drive cable 1816 between the shaft 1602 and the lower winding pulley 1810b.

The accumulator pulley 1812 may be arranged to receive and redirect the drive cable 1816 between the upper and lower winding pulleys 1810a,b. More specifically, in some embodiments, the upper and lower winding pulleys 1810a,b may be arranged for rotation in respective parallel planes, while the accumulator pulley 1812 may be arranged for rotation in a plane that is 90° offset from the parallel planes in order to redirect the drive cable 1816 between the upper and lower winding pulleys 1810a,b. In one embodiment, for example, the parallel planes of the upper and lower winding pulleys 1810a,b may be characterized as extending substantially horizontal, and the plane of the accumulator pulley 1812 may be characterized as extending substantially vertical and otherwise 90° offset from the horizontal planes. In other embodiments, however, the planes of the upper and lower winding pulleys 1810a,b and the accumulator pulley 1812 need not be 90° offset from each other. Moreover, the upper and lower winding pulleys 1810a,b need not be arranged for rotation in respective parallel planes, but may alternatively be arranged in non-parallel planes, without departing from the scope of the disclosure.

As mentioned above, the actuation system 1800 may be actuated or operated by rotating the first drive input 1620a, via operation of the first drive output 1718a (FIG. 17). Rotating the first drive input 1620a in a first angular direction C will correspondingly rotate the input stack 1802, including the accumulator 1804, in the same direction C and about the same rotational axis. Because the distal end 1820a of the drive cable 1816 is anchored to the shaft 1602 distal to the handle 1614, the drive cable 1816 may be drawn (pulled) into the accumulator 1804 at the upper winding pulley 1810a as the accumulator 1804 rotates in the direction C, as shown by the arrow D. Upon releasing the torque at the first drive input 1620a, or otherwise reversing the direction of the first drive output 1718a, the input stack 1802 will rotate opposite the direction C, and a length of the drive cable 1816 may correspondingly be paid out (fed) to the shaft 1602 from the upper winding pulley 1810a in a direction opposite the arrow D. Drawing the drive cable 1816 into the accumulator 1804 or paying out the drive cable 1816 from the accumulator 1804 may cause any of the operations of the surgical tool 1600 (FIGS. 16 and 17) described herein to occur. In at least one embodiment, however, actuation (operation) of the actuation system 1800 may result in the jaws 1610, 1612 (FIGS. 16-17) closing or opening, depending on the direction of the drive cable 1816.

The actuation system 1800 may also be decoupled from shaft 1602 insertion. More specifically, the winding pulleys 1810a,b, the accumulator pulley 1812, and the idler pulleys 1822a,b are able to freely rotate (e.g., "free wheel") and are otherwise not driven during operation of the handle 1614. Consequently, as the shaft 1602 moves longitudinally relative to the handle 1614 in z-axis translation, the drive cable 1816 is able to freely run (course) through the accumulator 1804 between the upper and lower idler pulleys 1822a,b. Moreover, since the winding pulleys 1810a,b, the accumulator pulley 1812, and the idler pulleys 1822a,b are able to freely rotate, the actuation system 1800 can be operated simultaneously during shaft 1602 translation.

In the illustrated embodiment, the input stack 1802 includes the first drive input 1620a, the drive shaft 1806 extending from the first drive input 1620a, and the accumulator 1804 mounted to the drive shaft 1806. Moreover, the accumulator 1804 comprises several component parts including the differential body 1808, the winding pulleys 1810a,b, and the accumulator pulley 1812. Furthermore, bearings (not shown) may be pressed into the differential body 1808 at the top and bottom of the input stack 1802 to facilitate rotation of the winding pulleys 1810a,b relative to the drive shaft 1806a, and a bearing (not shown) may be mounted to the lateral arm 1814 to rotatably mount the accumulator pulley 1812 to the differential body 1808. In some cases, various mechanical fasteners, such as c-clips or the like, are used to mount the accumulator 1804 to the drive shaft 1806 and also to mount the accumulator pulley 1812 to the lateral arm 1814. In other applications, the accumulator 1804 may be mounted to the drive shaft 1806 using screws with spacers, and the tightness of the screws may be set using a shim. Alternatively, this may be accomplished using screws on pulleys with bearings coupled with Belleville springs, wave springs, etc. to compress the inner race of the bearing. As will be appreciated, the high number of component parts increases the complexity and cost of the input stack 1802.

According to embodiments of the present disclosure, some or all of the component parts of the input stack 1802 may be molded or otherwise manufactured in a single, monolithic part, thereby significantly reducing part count and complexity of the input stack 1802.

Figure 19A:
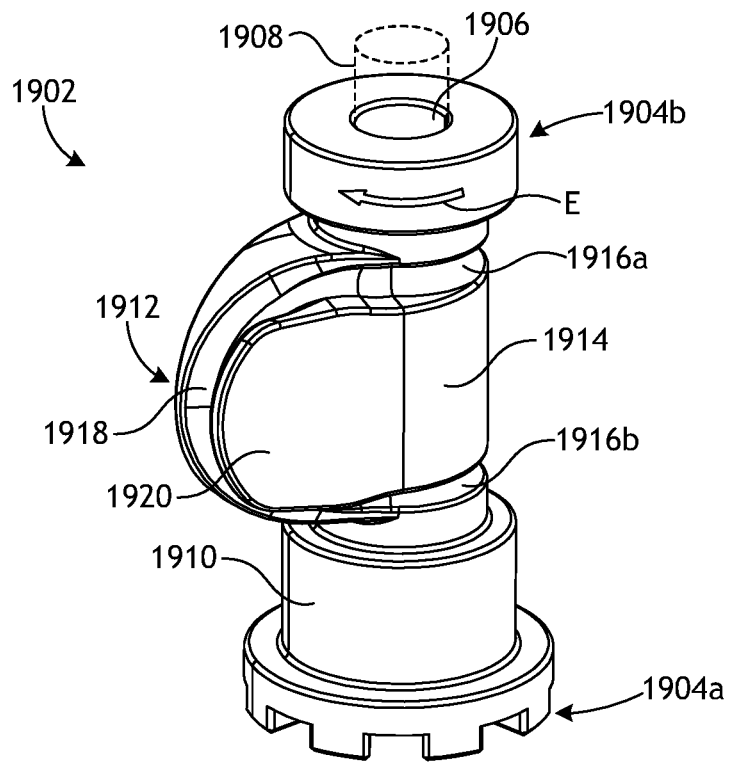
FIGS. 19A and 19B are left and right isometric views, respectively, of an example input stack that incorporates one or more embodiments of the present disclosure.
Figure 19B:
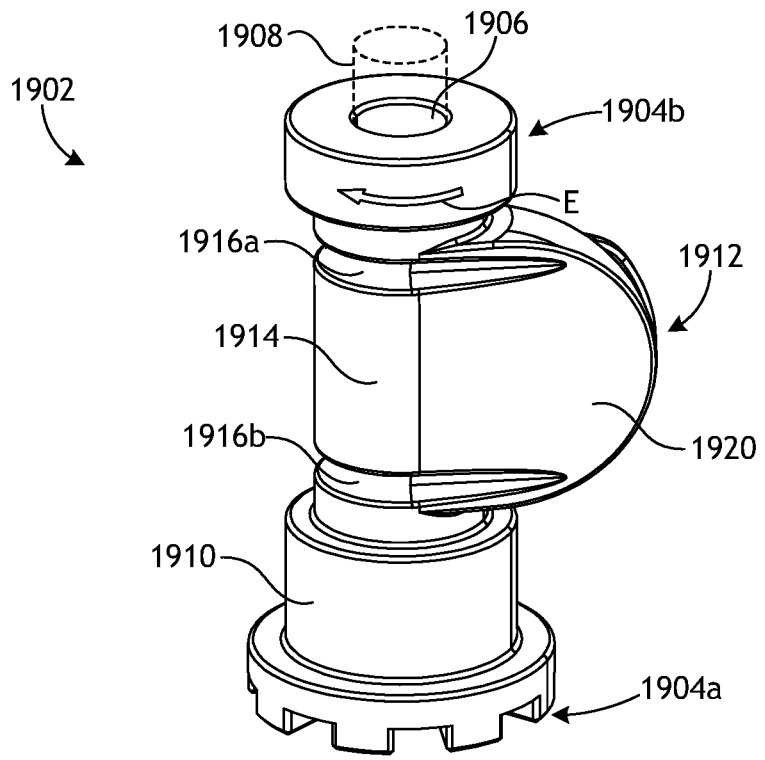

FIGS. 19A and 19B are left and right isometric views, respectively, of an example input stack 1902 that may incorporate one or more aspects of the present disclosure. The input stack 1902 may be similar in some respects to the input stack 1802 of FIG. 18 and may thus be used in conjunction with the actuation system 1800 (FIG. 18). In at least one embodiment, for instance, the input stack 1902 may replace the input stack 1802 in the actuation system 1800.

In the illustrated embodiment, the input stack 1902 comprises a generally cylindrical body having a first end 1904a and a second end 1904b opposite the first end 1904a. The input stack 1902 may be manufactured of a variety of rigid materials including, but not limited to, a metal (e.g., stainless steel, aluminum, etc.), a polymer (e.g., polyether ether ketone or "PEEK," glass-filled PEEK, nylon, polyetherimide or "PEI," polyoxymethylene or DELRIN® acetal homopolymer, etc.), a composite material, a ceramic (e.g., ceramic zirconia), or any combination thereof.

In some embodiments, a longitudinal channel 1906 may be defined through the body of the input stack 1902 and may extend longitudinally between the first and second ends 1904a,b. In some embodiments, the longitudinal channel 1906 does not extend all the way to the first end 1904a but instead stops short of the first end 1904a. In one or more embodiments, a support shaft 1908 (shown in dashed lines) may be received within the longitudinal channel 1906 and extend along all or a portion of the longitudinal channel 1906. The support shaft 1908 may be secured within the longitudinal channel 1906 in a variety of ways. In some embodiments, for example, the support shaft 1908 may be secured within the longitudinal channel 1906 using an adhesive or via welding or brazing. In other embodiments, the input stack 1902 may alternatively be overmolded onto the support shaft 1908. In yet further embodiments, the support shaft 1908 may be threaded into the longitudinal channel. The support shaft 1908 may be made of a rigid material, such as stainless steel, and may be configured to support and provide rigidity to the input stack 1902 during operation.

As illustrated, the input stack 1902 may include a drive input 1910 and an accumulator 1912. In the illustrated embodiment, the input stack 1902 comprise a monolithic structure, where the drive input 1910 and the accumulator 1912 form integral parts of the input stack 1902 and otherwise extend from each other to form portions (sections) of the whole. In such embodiments, the input stack 1902 may be manufactured via a variety of processes including, but not limited to, molding, overmolding, milling, forging, casting, three-dimensional (3D) printing, powdered metal compaction (e.g., powder metallurgy), or any combination thereof.

The drive input 1910 may be arranged at or near the first end 1904*a* of the input stack 1902. Moreover, the drive input 1902 may be the same as or similar to any of the drive inputs 1620*a-f* of FIGS. 16-17 and, therefore, may be matable with any of the drive outputs 1718*a-f* (FIG. 17) of the instrument driver 1618 (FIG. 17). Driving the drive input 1910 may correspondingly cause the input stack 1902 to rotate about a central axis.

The accumulator 1912 may be located between the first and second ends 1904*a,b* and extend from the drive input 1910. As illustrated, the accumulator 1912 may include a differential body 1914 that defines or otherwise provides a first or "upper" redirect surface 1916*a* and a second or "lower" redirect surface 1916*b*. The upper and lower redirect surfaces 1916*a,b* are axially offset from each other and comprise grooves or channels defined in the differential body 1914 and extending partially about the outer circumference of the differential body 1914.

As best seen in FIG. 19A, the accumulator 1912 may further include a redirect feature 1918 offset from the upper and lower redirect surfaces 1916*a,b*. The redirect feature 1918 may be provided on a lateral arm 1920 extending from the differential body 1914. In the illustrated embodiment, the redirect feature 1918 comprises a lateral redirect surface extending between and connecting the upper and lower redirect surfaces 1916*a,b*. More specifically, the redirect feature 1918 comprises a groove or a channel defined in the lateral arm 1920. Consequently, the upper and lower redirect surfaces 1916*a,b* and the redirect feature 1918 may cooperatively comprise a contiguous groove or channel defined in the differential body 1914.

The redirect surfaces 1916*a,b* and the redirect feature 1918 may be configured to receive a drive member, such as the drive cable 1816 of FIG. 18. In such embodiments, the drive cable 1816 may be routed or guided through the contiguous groove formed by the redirect surfaces 1916*a,b* and the redirect feature 1918. More specifically, the upper and lower redirect surfaces 1916*a,b* may extend about the outer circumference of the differential body 1914 in generally parallel planes, and the redirect feature 1918 may be arranged to receive and redirect the drive cable 1816 between the upper and lower redirect surfaces 1916*a,b*. In other embodiments, however, the redirect surfaces 1916*a,b* may extend about the outer circumference of the differential body 1914 in non-parallel planes, without departing from the scope of the disclosure.

In contrast to the upper and lower winding pulleys 1810*a,b* (FIG. 18) and the accumulator pulley 1812 (FIG. 18), which rotate during operation to feed the drive cable 1816 (FIG. 18) through the accumulator 1804 (FIG. 18), the redirect surfaces 1916*a,b* and the redirect feature 1918 comprise stationary (static) redirect features along (through) which the drive cable 1816 slides (traverses) during operation. Consequently, it may prove advantageous for the drive cable 1816 to be made of specialized materials that result in low frictional additions and minimal cable wear while translating (sliding) through the redirect surfaces 1916*a,b* and the redirect feature 1918. As indicated above, for example, the drive cable 1816 may be made of a polymer, such as ultra-high molecular weight polyethylene (UHMWPE, UHMW). In such embodiments, the UHMWPE may comprise a polymer braided cable, such as DYNEEMA® or SPECTRA®. In other embodiments, the drive cable 1816 may be made of a synthetic fiber, such as KEVLAR® or VECTRAN®. Moreover, in some embodiments, the drive cable 1816 may be coated with a lubricious material, such as, but not limited to, a titanium ceramic coating, a diamond-like carbon (DLC) coating, or any combination thereof.

Operation of the input stack 1902 is substantially similar to operation of the input stack 1802 of FIG. 18. Rotating the drive input 1910 in a first angular direction E will correspondingly rotate the entire input stack 1902 including the accumulator 1912, in the same direction E and thereby draw (pull) the drive cable 1816 (FIG. 18) into the accumulator 1912 at the upper redirect surface 1916*a*. Upon releasing the torque at the drive input 1910, or otherwise reversing direction of the drive input 1910, the input stack 1902 will rotate opposite the direction E, and a length of the drive cable 1816 may correspondingly be paid out (fed) to the shaft 1602 (FIG. 18) from the upper redirect surface 1916*a*.

When the input stack 1902 is not in use, the drive cable 1816 may be able to freely translate (slide) through the redirect surfaces 1916*a,b* and the redirect feature 1918. Consequently, as the shaft 1602 moves longitudinally relative to the handle 1614 (FIG. 18) in z-axis translation, the drive cable 1816 is able to freely run (course) through the accumulator 1912. Moreover, since the redirect surfaces 1916*a,b* and the redirect feature 1918 are decoupled from shaft 1602 insertion, the actuation system 1800 can be operated simultaneously during shaft 1602 translation.

Figure 20:
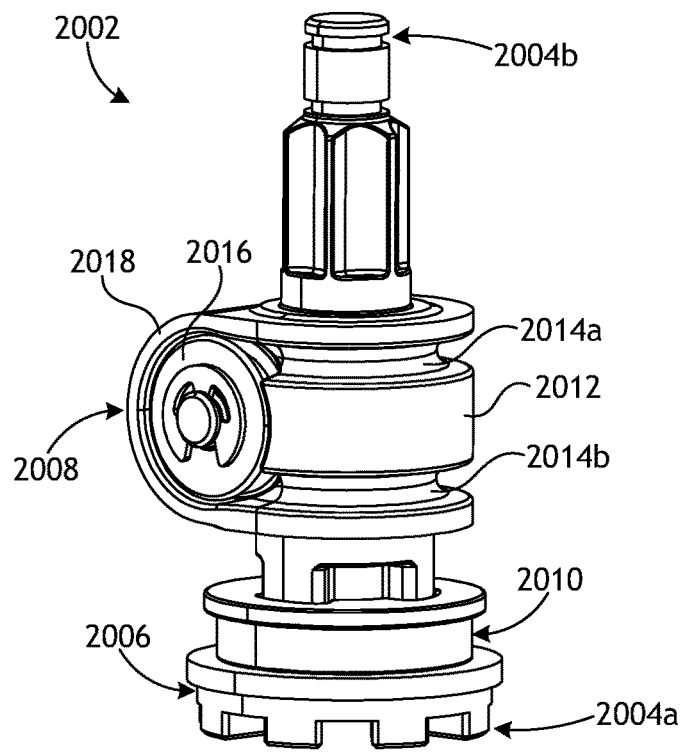
FIG. 20 is another example input stack that incorporates one or more embodiments of the present disclosure.

FIG. 20 is another example input stack 2002 that incorporates one or more embodiments of the present disclosure. The input stack 2002 may be similar in some respects to the input stacks 1802 and 1902 of FIGS. 18 and 19A-19B, respectively, and may thus be used in conjunction with the actuation system 1800 (FIG. 18) arranged within the handle 1614 (FIGS. 16-18). In at least one embodiment, for instance, the input stack 2002 may replace the input stack 1802 in the actuation system 1800.

The input stack 2002 has a first end 2004*a* and a second end 2004*b* opposite the first end 2004*a*. As illustrated, the input stack 2002 may include a drive input 2006, an accumulator 2008, and a decoupling ring 2010 that interposes the drive input 2006 and the accumulator 2008. The drive input 2006 may arranged at or near the first end 2004*a* and may be the same as or similar to any of the drive inputs 1620*a-f* of FIGS. 16-17. Consequently, the drive input 2006 may be matable with any of the drive outputs 1718*a-f* (FIG. 17) of the instrument driver 1618 (FIG. 17). Driving the drive input 2006 may correspondingly cause the entire input stack 2002 to rotate about a central axis.

The decoupling ring 2010 may operatively couple the accumulator 2008 to the drive input 2006 and may be axially movable between an engaged and a disengaged position. In the engaged position, the decoupling ring 2010 couples the accumulator 2008 to the drive input 2006 such that actuation of the drive input 2006 correspondingly rotates the accumulator 2008. Once moved to the disengaged position, however, the decoupling ring 2010 decouples (disengages) the accumulator 2008 from the drive input 2006, thus allowing the drive input 2006 to be back driven as necessary. Accordingly, when the decoupling ring 2010 is transitioned to the disengaged (decoupled) position, the drive input 2006 will be able to freely rotate. This may prove advantageous in a "bailout" state where an operator needs to disengage the motors and remove the loading of the end effector (e.g., in the event of a power loss while the end effector was engaging tissue, one would want to unload the jaws before removing the device). Disengaging also allows for back-driving the accumulator 2008 from the end effector.

In the illustrated embodiment, the drive input 2006, the accumulator 2008, and the decoupling ring 2010 comprise separate component parts of the input stack 2002. In at least one embodiment, however, the accumulator 2008 and the decoupling ring 2010 may comprise a monolithic component part of the input stack 2002 separate from the drive input 2006. In such embodiments, the combined accumulator 2008 and decoupling ring 2010 or the drive input 2006 may be axially actuatable relative to the other part to enable the input stack 2006 to transition between the engaged and disengaged states. In other embodiments, however, the drive input 2006 and the decoupling ring 2010 may comprise a monolithic part separate from the accumulator 2008. In such embodiments, the combined drive input 2006 and the decoupling ring 2010 or the accumulator 2008 be axially actuatable relative to the other part to enable the input stack 2006 to transition between the engaged and disengaged state. Portions of the input stack 2002 may be manufactured of the same materials mentioned above for the input stack 1902 of FIG. 19.

The accumulator 2008 may be located between the first and second ends 2004*a,b* and may include a differential body 2012 that defines or otherwise provides a first or "upper" redirect surface 2014*a* and a second or "lower" redirect surface 2014*b*. The upper and lower redirect surfaces 2014*a,b* are axially offset from each other and comprise grooves or channels defined in the differential body 2012 and extending partially about the outer circumference of the differential body 2012. The accumulator 2008 may further include a redirect feature 2016 offset from the upper and lower redirect surfaces 2014*a,b*. In the illustrated embodiment, the redirect feature 2016 may comprise a pulley rotatably mounted to a lateral arm 2018 extending from the differential body 2012. Moreover, the redirect feature 2016 may be configured to connect the upper and lower redirect surfaces 2014*a,b*.

The upper and lower redirect surfaces 2014*a,b* and the redirect feature 2016 may be configured to receive a drive member, such as the drive cable 1816 of FIG. 18. In such embodiments, the redirect feature 2016 may be arranged to receive and redirect the drive cable 1816 between the upper and lower redirect surfaces 2014*a,b*. Similar to the redirect surfaces 1916*a,b* of FIGS. 19A-19B, the redirect surfaces 2014*a,b* may comprise stationary (static) redirect features along (through) which the drive cable 1816 can slide during operation. In some embodiments, the redirect surfaces 2014*a,b* may extend about the outer circumference of the differential body 2012 in parallel planes, while the redirect feature 2016 may be arranged for rotation in a plane that is 90° offset from the parallel planes in order to redirect the drive cable 1816 between the upper and lower redirect surfaces 2014*a,b*. In one embodiment, for example, the parallel planes of the upper and lower redirect surfaces 2014*a,b* may be characterized as extending substantially horizontal, and the plane of the redirect feature 2016 may be characterized as extending substantially vertical and otherwise 90° offset from the horizontal planes. In other embodiments, however, the planes of the upper and lower redirect surfaces 2014*a,b* and the redirect feature 2016 need not be 90° offset from each other. Moreover, the redirect surfaces 2014*a,b* need not be defined in parallel planes, but may alternatively be defined in non-parallel planes, without departing from the scope of the disclosure.

Operation of the input stack 2002 is substantially similar to operation of the input stack 1902 of FIGS. 19A-19B, except that the drive cable 1816 (FIG. 18) is able to traverse the pulley redirect feature 2016 as it rotates during operation. Moreover, when the input stack 2002 is not in use, the drive cable 1816 may be able to translate (slide) through the upper and lower redirect surfaces 2014*a,b* and traverse the redirect feature 2016. Consequently, as the shaft 1602 (FIG. 18) moves longitudinally relative to the handle 1614 (FIG. 18) in z-axis translation, the drive cable 1816 is able to freely run (course) through the accumulator 2008. Moreover, since the upper and lower redirect surfaces 2014*a,b* and the redirect feature 2016 are decoupled from shaft 1602 insertion, the actuation system 1800 (FIG. 18) can be operated simultaneously during shaft 1602 translation.

Figure 21:
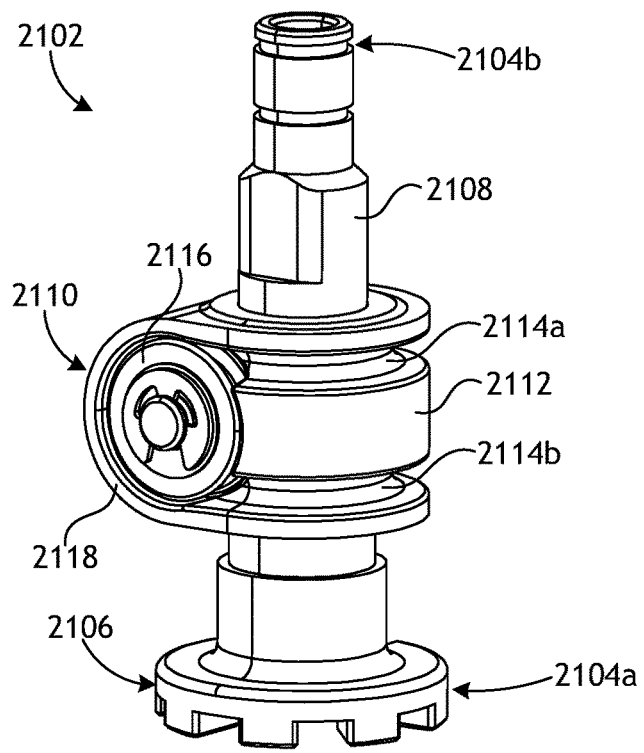
FIG. 21 is another example input stack that incorporates one or more embodiments of the present disclosure.

FIG. 21 is another example input stack 2102 that incorporates one or more embodiments of the present disclosure. The input stack 2102 may be similar in some respects to the input stack 1802 and 2002 of FIGS. 18 and 20, respectively, and may thus be used in conjunction with the actuation system 1800 (FIG. 18) arranged within the handle 1614 (FIGS. 16-18). In at least one embodiment, for instance, the input stack 2102 may replace the input stack 1802 in the actuation system 1800.

The input stack 2102 has a first end 2104*a* and a second end 2104*b* opposite the first end 2104*a*. As illustrated, the input stack 2102 may include a drive input 2106, a drive shaft 2108 extending from the drive input 2106, and an accumulator 2110. The various portions of the input stack 2102 may be manufactured of the same materials mentioned above for the input stack 1902 of FIG. 19. The drive input 2106 may be arranged at the first end 2104*a* and may be the same as or similar to any of the drive inputs 1620*a-f* of FIGS. 16-17. Consequently, the drive input 2106 may be matable with any of the drive outputs 1718*a-f* (FIG. 17) of the instrument driver 1618 (FIG. 17).

The drive shaft 2108 extends from the drive input 2106 and may, in some embodiments, form an integral extension of the drive input 2106. In other embodiments, however, the drive shaft 2108 may be coupled to the drive input 2106 as a separate component part of the input stack 2102. The accumulator 2110 may be coupled to the drive shaft 2108 such that rotating the drive shaft 2108 will correspondingly rotate the accumulator 2110 in the same direction about a central axis. In some embodiments, the accumulator 2110 may be coupled to the drive shaft 2108 using one or more mechanical fasteners such as, but not limited to, screws, pins, c-clips, or any combination thereof. In other embodiments, the accumulator 2110 may be coupled to the drive shaft 2108 through an interference or shrink fit engagement, via welding or brazing, or using an adhesive. In yet other embodiments, the accumulator 2110 may be coupled to the drive shaft 2108 by being overmolded onto the drive shaft 2108, without departing from the scope of the disclosure.

As illustrated, the accumulator 2110 may be located between the first and second ends 2104*a,b* and may include a differential body 2112 that defines or otherwise provides a first or "upper" redirect surface 2114*a* and a second or "lower" redirect surface 2114*b*. The upper and lower redirect surfaces 2114*a,b* are axially offset from each other and comprise grooves or channels defined in the differential body 2112 and extending partially about the outer circumference of the differential body 2112. The accumulator 2110 may further include a redirect feature 2116 offset from the upper and lower redirect surfaces 2114a,b. Similar to the redirect feature 2016 of FIG. 20, the redirect feature 2116 of the illustrated embodiment may comprise a pulley rotatably mounted to a lateral arm 2118 extending from the differential body 2212. The redirect feature 2216 may be configured to connect the upper and lower redirect surfaces 2114a,b.

Operation of the accumulator 2110 may be the same as or similar to operation of the accumulator 2008 of FIG. 20 and, therefore, will not be discussed again in detail.

Embodiments Disclosed Herein Include:

A. A robotic surgical tool that includes an elongate shaft extendable through a handle, a drive cable extending along a portion of the shaft, and an actuation system housed within the handle and including an input stack comprising a drive input arranged at a first end of the input stack, and an accumulator arranged between the first end and a second end of the input stack and including a differential body defining upper and lower redirect surfaces, and a redirect feature offset from the upper and lower redirect surfaces, wherein the drive cable extends through the upper and lower redirect surfaces and the redirect feature, and wherein actuating the actuation system rotates the input stack and thereby acts on the drive cable to cause one or more operations of the surgical tool.

B. A method of operating a robotic surgical tool that includes mating the robotic surgical tool with an instrument driver arranged at an end of a robotic arm, the robotic surgical tool including an elongate shaft extendable through a handle, a drive cable extending along a portion of the shaft, and an actuation system housed within the handle and including an input stack, the input stack comprising, a drive input arranged at a first end of the input stack, and an accumulator arranged between the first end and a second end of the input stack and including a differential body defining upper and lower redirect surfaces, and a redirect feature offset from the upper and lower redirect surfaces, wherein the drive cable extends through the upper and lower redirect surfaces and the redirect feature, actuating the actuation system to rotate the input stack and thereby act on the drive cable, and causing one or more operations of the surgical tool as the drive cable is drawn into or dispensed from the accumulator.

C. An input stack for a robotic surgical tool includes a drive input arranged at a first end of the input stack, an accumulator arranged between the first end and a second end of the input stack and including a differential body, upper and lower redirect surfaces defined in the differential body and comprising static grooves, and a redirect feature offset from and connecting the upper and lower redirect surfaces, wherein a drive cable is threadable through the accumulator by being received within the upper and lower redirect surfaces and the redirect feature.

Each of embodiments A, B, and C may have one or more of the following additional elements in any combination: Element 1: wherein the handle is matable with an instrument driver arranged at an end of a robotic arm, the instrument driver providing a drive output matable with the drive input, and wherein the shaft extends through the instrument driver via a central aperture defined longitudinally through the instrument driver. Element 2: wherein the input stack comprises a monolithic structure with the drive input and the accumulator forming integral parts of the input stack. Element 3: wherein the input stack is manufactured by a process selected from the group consisting of molding, overmolding, milling, forging, casting, three-dimensional printing, powdered metal compaction, and any combination thereof Element 4: wherein the upper and lower redirect surfaces and the redirect feature each comprise static grooves defined in the differential body, and wherein the redirect feature extends between and connects the upper and lower redirect surfaces. Element 5: wherein the upper and lower redirect surfaces comprise static grooves defined in the differential body and the redirect feature comprises a pulley rotatably mounted to the differential body. Element 6: wherein the input stack is made of a material selected from the group consisting of a metal, a polymer, a composite material, a ceramic and any combination thereof. Element 7: wherein the drive cable is made of a material selected from the group consisting of a polymer, a polymer braided cable, a synthetic fiber, and any combination thereof. Element 8: wherein the drive cable is coated with a lubricious material.

Element 9: wherein the upper and lower redirect surfaces and the redirect feature each comprise static grooves defined in the differential body, and wherein actuating the actuation system comprises sliding the drive cable through the upper and lower redirect surfaces and the redirect feature. Element 10: wherein the upper and lower redirect surfaces comprise static grooves defined in the differential body and the redirect feature comprises a pulley rotatably mounted to the differential body, and wherein actuating the actuation system further comprises sliding the drive cable through the upper and lower redirect surfaces, and feeding the drive cable through the pulley.

Element 11: wherein the drive input and the accumulator form a mono-lithic part. Element 12: wherein the monolithic part is made of a polymer selected from the group consisting of polyether ether ketone (PEEK), glass-filled PEEK, nylon, polyetherimide, polyoxymethylene, and any combination thereof. Element 13: wherein the redirect feature comprises a static groove de-fined in the differential body and extending between and connecting the upper and lower redirect surfaces. Element 14: wherein the redirect feature comprises a pulley rotatably mounted to the differential body. Element 15: wherein the input stack further comprises a decoupling ring that interposes the drive input and the accumulator. Element 16: wherein the input stack further comprises a drive shaft ex-tending from the drive input, and wherein the accumulator is coupled to the drive shaft. Element 17: wherein the input stack further comprises a longitudinal channel defined axially through the input stack, and a support shaft received within the longitudinal channel.

By way of non-limiting example, exemplary combinations applicable to A, B, and C include: Element 2 with Element 3; Element 2 with Element 4; Element 2 with Element 5; Element 3 with Element 4; Element 4 with Element 5; Element 4 with Element 6; Element 6 with Element 7; Element 11 with Element 12; Element 12 with Element 33; Element 12 with Element 14; and Element 12 with Element 15.

3. Implementing Systems and Terminology.

Implementations disclosed herein provide systems, methods and apparatus for instruments for use with robotic systems. It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

As used herein, the terms "generally" and "substantially" are intended to encompass structural or numeral modification which do not significantly affect the purpose of the element or number modified by such term.

To aid the Patent Office and any readers of this application and any resulting patent in interpreting the claims appended herein, applicants do not intend any of the appended claims or claim elements to invoke 35 U.S.C. 112(f) unless the words "means for" or "step for" are explicitly used in the particular claim.

The foregoing previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A robotic surgical tool, comprising:
    an elongate shaft extendable through a handle;
    a drive cable extending along a portion of the shaft; and
    an actuation system housed within the handle and including an input stack comprising:
        a drive input arranged at a first end of the input stack; and
        an accumulator arranged between the first end and a second end of the input stack and including a differential body defining upper and lower redirect surfaces, and a redirect feature offset from the upper and lower redirect surfaces,
    wherein the drive cable extends through the upper and lower redirect surfaces and the redirect feature, and wherein actuating the actuation system rotates the input stack and thereby acts on the drive cable to cause one or more operations of the surgical tool.

2. The robotic surgical tool of claim 1, wherein the handle is matable with an instrument driver arranged at an end of a robotic arm, the instrument driver providing a drive output matable with the drive input, and
    wherein the shaft extends through the instrument driver via a central aperture defined longitudinally through the instrument driver.

3. The robotic surgical tool of claim 1, wherein the input stack comprises a monolithic structure with the drive input and the accumulator forming integral parts of the input stack.

4. The robotic surgical tool of claim 3, wherein the input stack is manufactured by a process selected from the group consisting of molding, overmolding, milling, forging, casting, three-dimensional printing, powdered metal compaction, and any combination thereof.

5. The robotic surgical tool of claim 1, wherein the upper and lower redirect surfaces and the redirect feature each comprise static grooves defined in the differential body, and wherein the redirect feature extends between and connects the upper and lower redirect surfaces.

6. The robotic surgical tool of claim 1, wherein the upper and lower redirect surfaces comprise static grooves defined in the differential body and the redirect feature comprises a pulley rotatably mounted to the differential body.

7. The robotic surgical tool of claim 1, wherein the input stack is made of a material selected from the group consisting of a metal, a polymer, a composite material, a ceramic and any combination thereof.

8. The robotic surgical tool of claim 1, wherein the drive cable is made of a material selected from the group consisting of a polymer, a polymer braided cable, a synthetic fiber, and any combination thereof.

9. The robotic surgical tool of claim 1, wherein the drive cable is coated with a lubricious material.

10. A method of operating a robotic surgical tool, comprising:
    mating the robotic surgical tool with an instrument driver arranged at an end of a robotic arm, the robotic surgical tool including an elongate shaft extendable through a handle, a drive cable extending along a portion of the shaft, and an actuation system housed within the handle and including an input stack, the input stack comprising:
        a drive input arranged at a first end of the input stack; and
        an accumulator arranged between the first end and a second end of the input stack and including a differential body defining upper and lower redirect surfaces, and a redirect feature offset from the upper and lower redirect surfaces, wherein the drive cable extends through the upper and lower redirect surfaces and the redirect feature;
    actuating the actuation system to rotate the input stack and thereby act on the drive cable; and
    causing one or more operations of the surgical tool as the drive cable is drawn into or dispensed from the accumulator.

11. The method of claim 10, wherein the upper and lower redirect surfaces and the redirect feature each comprise static grooves defined in the differential body, and wherein actuating the actuation system comprises sliding the drive cable through the upper and lower redirect surfaces and the redirect feature.

12. The method of claim 10, wherein the upper and lower redirect surfaces comprise static grooves defined in the differential body and the redirect feature comprises a pulley rotatably mounted to the differential body, and wherein actuating the actuation system further comprises:

sliding the drive cable through the upper and lower redirect surfaces; and feeding the drive cable through the pulley.

13. An input stack for a robotic surgical tool, comprising:
a drive input arranged at a first end of the input stack;
an accumulator arranged between the first end and a second end of the input stack and including:
a differential body;
upper and lower redirect surfaces defined in the differential body and comprising static grooves; and
a redirect feature offset from and connecting the upper and lower redirect surfaces,
wherein a drive cable is threadable through the accumulator by being received within the upper and lower redirect surfaces and the redirect feature.

14. The input stack of claim 13, wherein the drive input and the accumulator form a monolithic part.

15. The input stack of claim 14, wherein the monolithic part is made of a polymer selected from the group consisting of polyether ether ketone (PEEK), glass-filled PEEK, nylon, polyetherimide, polyoxymethylene, and any combination thereof.

16. The input stack of claim 13, wherein the redirect feature comprises a static groove defined in the differential body and extending between and connecting the upper and lower redirect surfaces.

17. The input stack of claim 13, wherein the redirect feature comprises a pulley rotatably mounted to the differential body.

18. The input stack of claim 13, wherein the input stack further comprises a decoupling ring that interposes the drive input and the accumulator.

19. The input stack of claim 13, wherein the input stack further comprises a drive shaft extending from the drive input, and wherein the accumulator is coupled to the drive shaft.

20. The input stack of claim 13, wherein the input stack further comprises:
a longitudinal channel defined axially through the input stack; and
a support shaft received within the longitudinal channel.

* * * * *